United States Patent
Kovacs et al.

(10) Patent No.: US 9,149,429 B2
(45) Date of Patent: Oct. 6, 2015

(54) PREPARATIONS, METHODS AND KITS USEFUL FOR THE TREATMENT OF COUGH

(75) Inventors: Stephen Andras Kovacs, Loveland, OH (US); Jeffrey Alan Sargent, West Chester, OH (US); Helen Rochelle Kemp, Glendale, OH (US); Kristin Rhedrick Williams, West Chester, OH (US); Mary Lynn Jump, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 668 days.

(21) Appl. No.: 12/274,705

(22) Filed: Nov. 20, 2008

(65) Prior Publication Data

US 2009/0130199 A1 May 21, 2009

Related U.S. Application Data

(60) Provisional application No. 61/028,547, filed on Feb. 14, 2008, provisional application No. 61/003,886, filed on Nov. 21, 2007.

(51) Int. Cl.
- *A61K 9/00* (2006.01)
- *A61K 47/36* (2006.01)
- *A61K 47/38* (2006.01)

(52) U.S. Cl.
CPC .............. *A61K 9/006* (2013.01); *A61K 9/0073* (2013.01); *A61K 47/36* (2013.01); *A61K 47/38* (2013.01)

(58) Field of Classification Search
CPC ............................ A61K 9/006; A61K 9/0073
USPC ....................................... 424/455; 128/203.12
See application file for complete search history.

(56) References Cited

U.S. PATENT DOCUMENTS

| | | | |
|---|---|---|---|
| 5,196,436 A | 3/1993 | Smith | |
| 5,458,879 A * | 10/1995 | Singh et al. | 424/400 |
| 5,658,919 A | 8/1997 | Ratnaraj et al. | |
| 6,599,883 B1 | 7/2003 | Romeo et al. | |
| 6,699,502 B1 | 3/2004 | Fanara et al. | |
| 2005/0214349 A1 | 9/2005 | Nie et al. | |
| 2006/0039973 A1 | 2/2006 | Aldritt et al. | |
| 2006/0188450 A1 | 8/2006 | Clarot | |
| 2006/0216393 A1 | 9/2006 | Froseth et al. | |
| 2007/0148283 A1 | 6/2007 | Harvey et al. | |
| 2008/0026055 A1 | 1/2008 | Fubara et al. | |

FOREIGN PATENT DOCUMENTS

| | | |
|---|---|---|
| EP | 0306469 | 3/1989 |
| EP | 0387933 | 9/1990 |
| EP | 0552897 | 7/1993 |
| GB | 2328443 | 2/1999 |
| JP | H09-510703 T | 10/1997 |
| JP | 2005-505590 A | 2/2005 |
| JP | 2006-514077 T | 4/2006 |
| WO | WO 95/23591 | 9/1995 |
| WO | WO 96/23486 | 8/1996 |
| WO | WO 96/39116 | 12/1996 |
| WO | WO 00/44235 | 8/2000 |
| WO | WO 03/059085 | 7/2003 |
| WO | WO 2004/057979 | 7/2004 |
| WO | WO 2004/084637 | 10/2004 |
| WO | WO 2005/046347 | 5/2005 |
| WO | WO 2007/089652 | 8/2007 |
| WO | WO 2007/101115 | 9/2007 |

OTHER PUBLICATIONS

Gennaro et al, Remington's Pharmaceutical Sciences, Philadelphia College of Pharm. and Sci., 17th Ed., Chapter 84, pp. 1492-1517 (1985).*
Gennaro et al, "Solutions, Emulsions, Suspensions and Extracts," Remington's Pharmaceutical Sciences, Philadelphia College of Pharm. and Sci., 18th Ed., Chapter 83, pp. 1519-1544 (1990).*
Zicam Cough & Mist 8 hour max formula, www.Zicam.com/products/coughmax_spray.
Cepacol Dual Relief Spray, www. Cepacol.com/products/spray.asp.

* cited by examiner

*Primary Examiner* — Dennis J Parad
(74) *Attorney, Agent, or Firm* — Alexandra S. Anoff

(57) ABSTRACT

The invention relates to a respiratory preparation providing cough relief in a human comprising: a film forming agent; a thickening agent; and the respiratory preparation provides on demand relief. Additionally, the invention relates to a method of providing cough relief in a human comprising: the steps of administering to a human a respiratory preparation comprising: a film forming agent; a thickening agent; and wherein said respiratory preparation provides on demand cough relief as needed.

25 Claims, 13 Drawing Sheets

FIG. 1

| Table 1 | | | |
|---|---|---|---|
| Test Groups, Descriptions and Ingredients | | | |
| Test Group | Test Product | Usage | Test Product Ingredients |
| Reference Therapy | Reference Therapy® 300mg/100mL | Subjects swallowed 10mL at the beginning of the 4-hour observation period from a dosing cup. | Each 10mL contained 30mg dextromethorphan hydrobromide. Other ingredients included purified water, liquid maltitol, sodium benzoate, sodium saccharin, anhydrous citric acid, punch flavor. |
| Water Control | Filtered water in a spray bottle[b] | Subjects used each time they felt the urge to cough throughout the 4-hour observation period. Each usage consisted of 3 sprays into the mouth (each spray 0.14 - 0.16mL). | Chlorinated water run through a 0.2 micron filter. |
| Respiratory preparation 1 | In a spray bottle[b] | Subjects used each time they felt the urge to cough throughout the 4-hour observation period. Each usage consisted of 3 sprays into the mouth (each spray 0.14 - 0.16mL). | Water, propylene glycol, sorbitol, carboxymethylcellulose sodium, sucralose, benzoic acid, sodium benzoate, honey lemon flavor (FLV Honey Lemon AF1266/115101H).. |
| Respiratory preparation 2 | In a spray bottle[b] | Subjects used each time they felt the urge to cough throughout the 4-hour observation period. Each usage consisted of 3 sprays into the mouth (each spray 0.14 - 0.16mL). | Water, propylene glycol, sorbitol, carboxymethylcellulose sodium, polyoxyl 40 stearate, polyethylene oxide, sucralose, benzoic acid, sodium benzoate, honey lemon flavor (FLV Honey Lemon AF1266/115101H). |
| No Treatment Control | None | Not Applicable | Not Applicable |
| [b] The bottle was a 30mL round transparent bottle made of polyethylene terephthalate (PET) with a 24-410 closure.(drawing number 22759) manufactured by Wheaton Plastics, a division of Alcan Packaging. The spray pump was the Mark VI fine mist sprayer with a 24-410 closure and standard head manufactured by Calmar, a MeadWestvaco Company. | | | |

FIG. 2

| Table 2 | |
|---|---|
| Number of Subjects randomized to Treatment Groups | |
| Treatment Groups | Number of subjects |
| Water Control | 40 |
| Reference Therapy | 42 |
| Respiratory preparation 1 | 41 |
| Respiratory preparation 2 | 42 |
| No Treatment Control | 10 |
| Total | 175 |

FIG. 3

Table 3
Respiratory preparation 1 Versus No Treatment Control with Respect to Efficacy Parameters (Evaluable Subjects)

| Efficacy Parameter | Time | No Treatment Control | | Resp. Prep. 1 | | One-sided p-value[b] |
| --- | --- | --- | --- | --- | --- | --- |
| | | N | Mean / Median[a] | N | Mean / Median[a] | |
| Number of Coughs | Hour 1 | 10 | 32 | 40 | 13 | 0.2733 |
| | Hour 2 | 10 | 29 | 39 | 11 | 0.0592[c] |
| | Hour 3 | 10 | 27 | 39 | 13 | 0.0270[c] |
| | Hour 4 | 10 | 19 | 38 | 7 | 0.0356 |
| | Hours 1-4 | 10 | 110 | 40 | 54 | 0.0776[c] |
| Number of Cough Bouts | Hour 1 | 10 | 20 | 40 | 9 | 0.1898 |
| | Hour 2 | 10 | 19 | 39 | 9 | 0.0421[c] |
| | Hour 3 | 10 | 17 | 39 | 7 | 0.0325[c] |
| | Hour 4 | 10 | 13 | 38 | 5 | 0.0295[c] |
| | Hours 1-4 | 10 | 65 | 40 | 34 | 0.0727[c] |
| Perceived Cough Frequency | Hour 1 | 10 | 4.3 | 38 | 3.7 | 0.1315 |
| | Hour 2 | 10 | 3.6 | 40 | 2.7 | 0.0187[c] |
| | Hour 3 | 10 | 3.5 | 39 | 2.5 | 0.0148[c] |
| | Hour 4 | 10 | 3.2 | 40 | 2.1 | 0.0027[c] |
| | Average | 10 | 3.7 | 37 | 2.7 | 0.0085[c] |
| Perceived Cough Severity | Hour 1 | 10 | 3.7 | 38 | 3.1 | 0.0536[c] |
| | Hour 2 | 10 | 3.5 | 39 | 2.5 | 0.0081[c] |
| | Hour 3 | 10 | 3.2 | 40 | 2.2 | 0.0037[c] |
| | Hour 4 | 10 | 3.1 | 40 | 1.9 | 0.0013[c] |
| | Average | 10 | 3.4 | 37 | 2.4 | 0.0032[c] |

N = number of subjects in category
Median for Number of Coughs and Number of Cough Bouts and mean for other efficacy parameters.
One-sided p-value for Wilcoxon Rank Sum test to compare treatments.
Statistically significant differences ($\alpha < 0.10$)

FIG. 4

| Table 4 | | | | | | |
|---|---|---|---|---|---|---|
| Respiratory preparation 1 Versus Water Control with Respect to Efficacy Parameters | | | | | | |
| (Evaluable Subjects) | | | | | | |
| | | Water Control | | Resp. Prep. 1 | | |
| Efficacy Parameter | Time | N | Mean/Median[a] | N | Mean/Median[a] | One-sided p-value[b] |
| Number of Coughs | Hour 1 | 34 | 16 | 40 | 13 | 0.7893 |
| | Hour 2 | 34 | 16 | 39 | 11 | 0.2270 |
| | Hour 3 | 33 | 13 | 39 | 13 | 0.4240 |
| | Hour 4 | 34 | 9 | 38 | 7 | 0.2425 |
| | Hours 1-4 | 34 | 55 | 40 | 54 | 0.5623 |
| Number of Cough Bouts | Hour 1 | 34 | 10 | 40 | 9 | 0.7468 |
| | Hour 2 | 34 | 8 | 39 | 9 | 0.3256 |
| | Hour 3 | 33 | 7 | 39 | 7 | 0.5270 |
| | Hour 4 | 34 | 7 | 38 | 5 | 0.2961 |
| | Hours 1-4 | 34 | 30 | 40 | 34 | 0.6808 |
| Perceived Cough Frequency | Hour 1 | 34 | 3.5 | 38 | 3.7 | 0.7159 |
| | Hour 2 | 34 | 3.0 | 40 | 2.7 | 0.2089 |
| | Hour 3 | 34 | 2.7 | 39 | 2.5 | 0.2066 |
| | Hour 4 | 34 | 2.3 | 40 | 2.1 | 0.0356[c] |
| | Average | 34 | 2.9 | 37 | 2.7 | 0.2901 |
| Perceived Cough Severity | Hour 1 | 34 | 3.0 | 38 | 3.1 | 0.6601 |
| | Hour 2 | 34 | 2.9 | 39 | 2.5 | 0.0917[c] |
| | Hour 3 | 34 | 2.4 | 40 | 2.2 | 0.1363 |
| | Hour 4 | 34 | 2.4 | 40 | 1.9 | 0.0043[c] |
| | Average | 34 | 2.7 | 37 | 2.4 | 0.0846[c] |
| Perceived Onset of Cough Relief | Final | 34 | 3.0 | 40 | 4.0 | 0.0397[c] |
| Perceived Duration of Cough Relief | Final | 34 | 3.6 | 40 | 3.5 | 0.5197 |
| Perceived Level of Cough Relief | Final | 34 | 3.7 | 40 | 4.7 | 0.0203[c] |
| Perceived Level of Throat Coating | Final | 34 | 3.5 | 40 | 4.8 | 0.0059[c] |
| = number of subjects in category | | | | | | |
| Median for Number of Coughs and Number of Cough Bouts and mean for other efficacy parameters. | | | | | | |
| One-sided p-value for Wilcoxon Rank Sum test to compare treatments. | | | | | | |
| Statistically significant differences ($\alpha < 0.10$) | | | | | | |

FIG. 5

Table 5
Respiratory preparation 1 Versus Reference Therapy with Respect to Efficacy Parameters
(Evaluable Subjects)

| Efficacy Parameter | Time | Reference Therapy | | Resp. Prep. 1 | | One-sided p-value[b] |
| --- | --- | --- | --- | --- | --- | --- |
| | | N | Mean / Median[a] | N | Mean /Median[a] | |
| Number of Coughs | Hour 1 | 39 | 13 | 40 | 13 | 0.5448 |
| | Hour 2 | 37 | 10 | 39 | 11 | 0.7191 |
| | Hour 3 | 39 | 7 | 39 | 13 | 0.7843 |
| | Hour 4 | 39 | 5 | 38 | 7 | 0.6983 |
| | Hours 1-4 | 39 | 44 | 40 | 54 | 0.7372 |
| Number of Cough Bouts | Hour 1 | 39 | 7 | 40 | 9 | 0.6648 |
| | Hour 2 | 37 | 6 | 39 | 9 | 0.8062 |
| | Hour 3 | 39 | 4 | 39 | 7 | 0.8110 |
| | Hour 4 | 39 | 3 | 38 | 5 | 0.7775 |
| | Hours 1-4 | 39 | 30 | 40 | 34 | 0.7992 |
| Perceived Cough Frequency | Hour 1 | 38 | 3.3 | 38 | 3.7 | 0.8887 |
| | Hour 2 | 38 | 2.8 | 40 | 2.7 | 0.4326 |
| | Hour 3 | 39 | 2.2 | 39 | 2.5 | 0.8462 |
| | Hour 4 | 39 | 2.0 | 40 | 2.1 | 0.4206 |
| | Average | 38 | 2.5 | 37 | 2.7 | 0.7962 |
| Perceived Cough Severity | Hour 1 | 38 | 2.7 | 38 | 3.1 | 0.9240 |
| | Hour 2 | 38 | 2.4 | 39 | 2.5 | 0.5689 |
| | Hour 3 | 39 | 2.0 | 40 | 2.2 | 0.7971 |
| | Hour 4 | 39 | 1.9 | 40 | 1.9 | 0.3579 |
| | Average | 38 | 2.3 | 37 | 2.4 | 0.6841 |

N = number of subjects in category
[a] Median for Number of Coughs and Number of Cough Bouts and mean for other efficacy parameters.
[b] One-sided p-value for Wilcoxon Rank Sum test to compare treatments.

FIG. 6

Table 6

Respiratory preparation 2 Versus No Treatment Control with Respect to Efficacy Parameters (Evaluable Subjects)

| Efficacy Parameter | Time | No Treatment Control | | Resp. Prep. 2 | | One-sided p-value[b] |
| --- | --- | --- | --- | --- | --- | --- |
| | | N | Mean / Median[a] | N | Mean /Median[a] | |
| Number of Coughs | Hour 1 | 10 | 32 | 40 | 9 | 0.0563 |
| | Hour 2 | 10 | 29 | 40 | 5 | 0.0065 |
| | Hour 3 | 10 | 27 | 39 | 8 | 0.0062 |
| | Hour 4 | 10 | 19 | 40 | 4 | 0.0091 |
| | Hours 1-4 | 10 | 110 | 40 | 34 | 0.0131 |
| Number of Cough Bouts | Hour 1 | 10 | 20 | 40 | 6 | 0.0373 |
| | Hour 2 | 10 | 19 | 40 | 3 | 0.0047 |
| | Hour 3 | 10 | 17 | 39 | 4 | 0.0066 |
| | Hour 4 | 10 | 13 | 40 | 3 | 0.0049 |
| | Hours 1-4 | 10 | 65 | 40 | 20 | 0.0089 |
| Perceived Cough Frequency | Hour 1 | 10 | 4.3 | 40 | 3.2 | 0.0195 |
| | Hour 2 | 10 | 3.6 | 40 | 2.4 | 0.0043 |
| | Hour 3 | 10 | 3.5 | 40 | 2.3 | 0.0030 |
| | Hour 4 | 10 | 3.2 | 40 | 2.1 | 0.0036 |
| | Average | 10 | 3.7 | 40 | 2.5 | 0.0014 |
| Perceived Cough Severity | Hour 1 | 10 | 3.7 | 40 | 3.0 | 0.0412 |
| | Hour 2 | 10 | 3.5 | 40 | 2.4 | 0.0038 |
| | Hour 3 | 10 | 3.2 | 40 | 2.3 | 0.0053 |
| | Hour 4 | 10 | 3.1 | 40 | 2.0 | 0.0022 |
| | Average | 10 | 3.4 | 40 | 2.4 | 0.0032 |

N = number of subjects in category
[a] Median for Number of Coughs and Number of Cough Bouts and mean for other efficacy parameters.
[b] One-sided p-value for Wilcoxon Rank Sum test to compare treatments; statistically significant differences ($\alpha < 0.10$).

FIG. 7

Table 7
Respiratory preparation 2 Versus Water Control with Respect to Efficacy Parameters
(Evaluable Subjects)

| Efficacy Parameter | Time | Water Control | | Resp. Prep. 2 | | One-sided p-value[b] |
|---|---|---|---|---|---|---|
| | | N | Mean / Median[a] | N | Mean / Median[a] | |
| Number of Coughs | Hour 1 | 34 | 16 | 40 | 9 | 0.1078 |
| | Hour 2 | 34 | 16 | 40 | 5 | 0.0037[c] |
| | Hour 3 | 33 | 13 | 39 | 8 | 0.0676[c] |
| | Hour 4 | 34 | 9 | 40 | 4 | 0.0406[c] |
| | Hours 1-4 | 34 | 55 | 40 | 34 | 0.0297[c] |
| Number of Cough Bouts | Hour 1 | 34 | 10 | 40 | 6 | 0.1669 |
| | Hour 2 | 34 | 8 | 40 | 3 | 0.0037[c] |
| | Hour 3 | 33 | 7 | 39 | 4 | 0.1352 |
| | Hour 4 | 34 | 7 | 40 | 3 | 0.0220[c] |
| | Hours 1-4 | 34 | 30 | 40 | 20 | 0.0444[c] |
| Perceived Cough Frequency | Hour 1 | 34 | 3.5 | 40 | 3.2 | 0.2645 |
| | Hour 2 | 34 | 3.0 | 40 | 2.4 | 0.0323[c] |
| | Hour 3 | 34 | 2.7 | 40 | 2.3 | 0.0738[c] |
| | Hour 4 | 34 | 2.3 | 40 | 2.1 | 0.0995[c] |
| | Average | 34 | 2.9 | 40 | 2.5 | 0.0902[c] |
| Perceived Cough Severity | Hour 1 | 34 | 3.0 | 40 | 3.0 | 0.4121 |
| | Hour 2 | 34 | 2.9 | 40 | 2.4 | 0.0314[c] |
| | Hour 3 | 34 | 2.4 | 40 | 2.3 | 0.1967 |
| | Hour 4 | 34 | 2.4 | 40 | 2.0 | 0.0278[c] |
| | Average | 34 | 2.7 | 40 | 2.4 | 0.1011 |
| Perceived Onset of Cough Relief | Final | 34 | 3.0 | 40 | 3.8 | 0.0590[c] |
| Perceived Duration of Cough Relief | Final | 34 | 3.6 | 40 | 4.1 | 0.1052 |
| Perceived Level of Cough Relief | Final | 34 | 3.7 | 40 | 4.9 | 0.0024[c] |
| Perceived Level of Throat Coating | Final | 34 | 3.5 | 40 | 4.8 | 0.0035[c] |

N = number of subjects in category
Median for Number of Coughs and Number of Cough Bouts and mean for other efficacy parameters.
One-sided p-value for Wilcoxon Rank Sum test to compare treatments.
Statistically significant differences ($\alpha < 0.10$)

FIG. 8

| Table 8 | | | | | | |
|---|---|---|---|---|---|---|
| Respiratory preparation 2 Versus Reference Therapy with Respect to Efficacy Parameters | | | | | | |
| (Evaluable Subjects) | | | | | | |
| | | Reference Therapy | | Resp. Prep. 2 | | |
| Efficacy Parameter | Time | N | Mean / Median[a] | N | Mean /Median[a] | One-sided p-value[b] |
| Number of Coughs | Hour 1 | 39 | 13 | 40 | 9 | 0.0637[c] |
| | Hour 2 | 37 | 10 | 40 | 5 | 0.0532[c] |
| | Hour 3 | 39 | 7 | 39 | 8 | 0.3340 |
| | Hour 4 | 39 | 5 | 40 | 4 | 0.3085 |
| | Hours 1-4 | 39 | 44 | 40 | 34 | 0.1486 |
| Number of Cough Bouts | Hour 1 | 39 | 7 | 40 | 6 | 0.0935[c] |
| | Hour 2 | 37 | 6 | 40 | 3 | 0.0669[c] |
| | Hour 3 | 39 | 4 | 39 | 4 | 0.3689 |
| | Hour 4 | 39 | 3 | 40 | 3 | 0.2599 |
| | Hours 1-4 | 39 | 30 | 40 | 20 | 0.2132 |
| Perceived Cough Frequency | Hour 1 | 38 | 3.3 | 40 | 3.2 | 0.4855 |
| | Hour 2 | 38 | 2.8 | 40 | 2.4 | 0.1139 |
| | Hour 3 | 39 | 2.2 | 40 | 2.3 | 0.7277 |
| | Hour 4 | 39 | 2.0 | 40 | 2.1 | 0.6792 |
| | Average | 38 | 2.5 | 40 | 2.5 | 0.4441 |
| Perceived Cough Severity | Hour 1 | 38 | 2.7 | 40 | 3.0 | 0.7363 |
| | Hour 2 | 38 | 2.4 | 40 | 2.4 | 0.3714 |
| | Hour 3 | 39 | 2.0 | 40 | 2.3 | 0.8687 |
| | Hour 4 | 39 | 1.9 | 40 | 2.0 | 0.7044 |
| | Average | 38 | 2.3 | 40 | 2.4 | 0.7329 |
| N = number of subjects in category | | | | | | |
| Median for Number of Coughs and Number of Cough Bouts and mean for other efficacy parameters. | | | | | | |
| One-sided p-value for Wilcoxon Rank Sum test to compare treatments. | | | | | | |
| Statistically significant differences ($\alpha < 0.10$) | | | | | | |

FIG. 9

| Table 9 Device | Batch # | Ingredients |
|---|---|---|
| Respiratory Preparation | HCF164-038D | Water, propylene glycol, sorbitol, carboxymethylcellulose sodium, polyoxyl 40 stearate, polyethylene oxide, sucralose, benzoic acid, sodium benzoate, honey lemon flavor (FLV Honey Lemon AF1266/115101H). |
| (Reference Medical Device)a | NA | Water, sorbitol, carboxymethylcellulose, sodium, methylparaben, propylparaben, potassium chloride, dibasic sodium phosphate, calcium chloride, magnesium chloride, sodium chloride, flavor. |
| [a] Commercially available product distributed by Kingswood Laboratories, Inc. Indianapolis, IN. |||

FIG. 10

| | Table 10 Respiratory preparation |
|---|---|---|
| Respiratory preparation | Batch # | Respiratory Preparation Ingredients |
| Respiratory preparation 2 | HCF164-038D | Water, propylene glycol, sorbitol, carboxymethylcellulose sodium, polyoxyl 40 stearate, polyethylene oxide, sucralose, benzoic acid, sodium benzoate, honey lemon flavor (FLV Honey Lemon AF1266/115101H). |
| | The Respiratory Preparation was contained in spray bottles, and the bottle was a 30 mL round transparent bottle made of polyethylene terephthalate (PET) with a 24-410 closure (drawing number 22759) manufactured by Wheaton Plastics, a division of Alcan Packaging. The spray pump was the Mark VI fine mist sprayer with a 24-410 closure and standard head manufactured by Calmar, a MeadWestvaco Company. |

FIG. 11

| Table 11 | | |
|---|---|---|
| Area Under the Retained Fraction Versus Time Curve From 0 to 1 Hour | | |
| By Region of Interest | | |
| Technetium-99m | | |
| Region of Interest | Descriptive Statistic | Value |
| Oral Cavity | N | 16 |
|  | Mean (STD) | 3.36 (2.45) |
|  | Median | 3.13 |
|  | Minimum - Maximum | 0.24 - 8.30 |
|  | 95% Confidence Interval Mean | (2.06, 4.67) |
| Proximal Oropharynx | N | 16 |
|  | Mean (STD) | 1.83 (1.15) |
|  | Median | 1.48 |
|  | Minimum - Maximum | 0.42 - 4.18 |
|  | 95% Confidence Interval Mean | (1.22, 2.45) |
| Total Oropharynx | N | 16 |
|  | Mean (STD) | 6.01 (3.93) |
|  | Median | 5.28 |
|  | Minimum - Maximum | 1.02 - 15.43 |
|  | 95% Confidence Interval Mean | (3.91, 8.10) |
| Esophagus | N | 16 |
|  | Mean (STD) | 1.52 (0.69) |
|  | Median | 1.55 |
|  | Minimum - Maximum | 0.34 - 2.91 |
|  | 95% Confidence Interval Mean | (1.15, 1.89) |
| N = number of subjects | | |
| STD = standard deviations | | |
| Units for all descriptive statistics except N are minutes. | | |

FIG. 12

| Table 12 Area Under the Retained Fraction Versus Time Curve From 0 to 1 Hour By Region of Interest Indium DTPA |||
|---|---|---|
| Region of Interest | Descriptive Statistic | Value |
| Oral Cavity | N | 16 |
|  | Mean (STD) | 2.69 (1.90) |
|  | Median | 2.15 |
|  | Minimum - Maximum | 0.17 - 6.39 |
|  | 95% Confidence Interval Mean | (1.68, 3.70) |
| Proximal Oropharynx | N | 16 |
|  | Mean (STD) | 1.63 (1.01) |
|  | Median | 1.31 |
|  | Minimum - Maximum | 0.17 - 3.38 |
|  | 95% Confidence Interval Mean | (1.09, 2.17) |
| Total Oropharynx | N | 16 |
|  | Mean (STD) | 5.83 (4.06) |
|  | Median | 4.54 |
|  | Minimum - Maximum | 1.19 - 15.92 |
|  | 95% Confidence Interval Mean | (3.66, 7.99) |
| Esophagus | N | 16 |
|  | Mean (STD) | 1.41 (0.67) |
|  | Median | 1.37 |
|  | Minimum - Maximum | 0.43 - 3.01 |
|  | 95% Confidence Interval Mean | (1.05, 1.77) |

N = number of subjects
STD = standard deviations
Units for all descriptive statistics except N are minutes.

PREPARATIONS, METHODS AND KITS USEFUL FOR THE TREATMENT OF COUGH

CROSS REFERENCE TO RELATED APPLICATIONS

This reference claims the benefit of U.S. Provisional Application No. 61/028,547, filed Feb. 18, 2008, and U.S. Provisional Application No. 61,003,886, filed Nov. 21, 2007.

FIELD OF THE INVENTION

The invention relates to a respiratory preparation providing cough relief in a human comprising: a film forming agent; a thickening agent; and wherein said respiratory preparation provides on demand relief as needed.

BACKGROUND OF THE INVENTION

Post nasal drip is caused by the over secretion of mucous in the nasal cavity. The constant trickle of mucus in the throat results in triggering the cough reflex. During colds (viral infections), inflammation may occur in the mucosa such that cytokines and inflammatory mediators are released into nasal secretions. These then bathe the throat and cause a sequence of pain/soreness that is much more easily aggravated by innocuous stimuli such as changes in air temperature (cold air) which stimulate the cough reflex. Additionally, the cough reflex can also be stimulated by a dry mouth and/or throat. Desensitization of the cough receptors in the throat is believed to provide antitussive effect via the mechanical action of shielding the receptors from further irritation. Cough receptors have been identified functionally and are present on the sensory nerve endings within the epithelium lining in the larynx and pharynx.

Attempts have been made to alleviate this cough response by compositions such as cough drops, sore throat sprays, and cough syrups. The response of current cough drops is not instant and drops are usually solid doses that must be melted in the mouth and provide no coating of the throat. Sore throat sprays can contain actives that numb the mouth and throat. Sprays normally contain instruction to not swallow so there is no throat coating and no cough relief. Additionally, because they normally contain actives the product cannot be used often as needed. Cough syrups contain actives that must be absorbed by the blood which usually takes about 30 minutes for any type of cough relief, therefore there is no instant relief that is targeted for the throat.

Additionally, it is believed that cough suppression can be enhanced by focused delivery of the active to the site of irritation, the target mucosa. The benefit of targeted delivery such as that which is realized when a spray is used, is that the actives are not lost to irreversible binding to the mucin (via mucoadhesion) before they can reach the target sites.

Therefore, the various embodiments described herein provide for a respiratory preparation that provides instant and on demand cough relief in a portable form that can be used as often as needed. The preparation can be used to target the mouth and/or throat and provide a protective barrier that shields the epithelial cells that line the throat and thus prevents the stimulation of a cough response and/or triggers the flow of saliva and to help to hydrate the mouth and/or throat. The barrier can additionally aid in reducing inflammation of the mouth and/or throat and relive minor pain sometimes associated with a cough and/or sore throat.

SUMMARY OF THE INVENTION

One embodiment is directed to a respiratory preparation providing cough relief in a human comprising: a film forming agent; a thickening agent; and wherein said respiratory preparation provides on demand relief.

An additional embodiment further relates to a method of providing cough relief in a human comprising: the steps of administering to a human a respiratory preparation comprising: a film forming agent; a thickening agent; and wherein said respiratory preparation provides on demand cough relief.

An additional embodiment is further directed to a kit comprising: a delivery device and a respiratory preparation contained in said delivery device; wherein said respiratory preparation comprising: a film forming agent; a thickening agent; and wherein said respiratory preparation provides on demand cough relief.

BRIEF DESCRIPTION OF THE DRAWINGS

FIG. 1 is a Table and shows a description of the test groups and brief usage instructions;

FIG. 2 is a Table and shows a description of the Number of Subjects randomized to Treatment Groups;

FIG. 3 is a Table and shows a description of the summary of efficacy results for the Respiratory preparation 1 vs. No Treatment Control;

FIG. 4 is a Table and shows a description of the summary of efficacy results for the Respiratory preparation 1 vs. Water Control;

FIG. 5 is a Table and shows a description of the all one-sided comparisons of Respiratory preparation 1 versus the Reference Therapy;

FIG. 6 is a Table and shows a description of the summary efficacy results for the Respiratory preparation 2 vs. No Treatment Control;

FIG. 7 is a Table and shows a description of the summary efficacy results for the Respiratory preparation 2 vs. Water Control;

FIG. 8 is a Table and shows a description of the summary efficacy results for the Respiratory preparation 2 vs. Reference Therapy;

FIG. 9 is a Table and shows a description of the Respiratory preparation and Reference Medical Device;

FIG. 10 is a Table and shows a description of the Respiratory preparation;

FIG. 11 is a Table and shows the descriptive statistics and 95% confidence intervals for the mean of each scintigraphy parameter for Technetium-99m;

FIG. 12 is a Table and shows the descriptive statistics and 95% confidence intervals for the mean of each scintigraphy parameter for Indium DTPA.

DETAILED DESCRIPTION OF THE INVENTION

Figure 13:
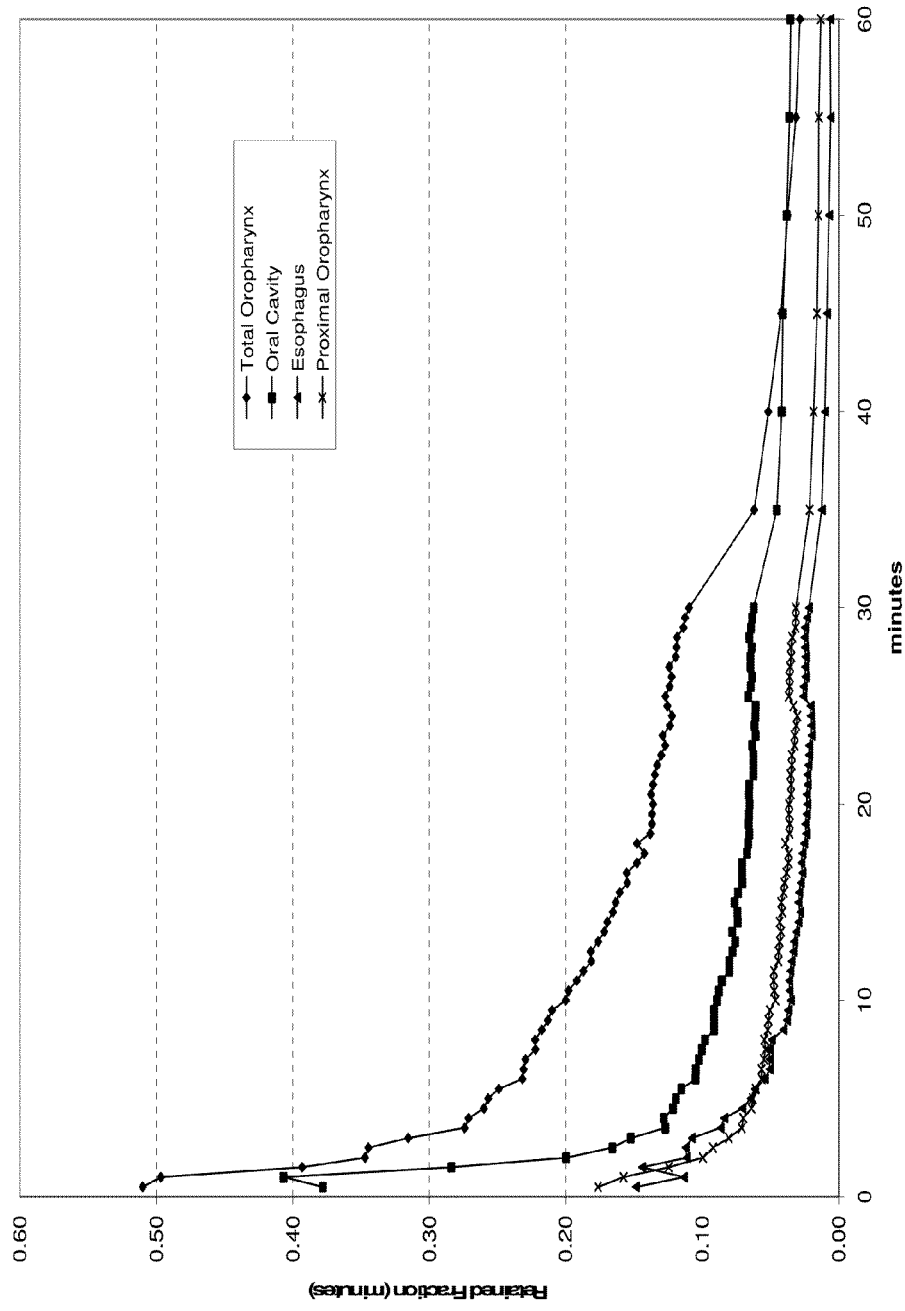
FIG. 13 is a graphical depiction of the area under the retained volume versus time curve from 0 to 1 hour by region of interest.

One embodiment is directed to a respiratory preparation providing cough relief in a human comprising: a film forming agent; a thickening agent; and wherein said respiratory preparation provides on demand relief.

These and other limitations of the compositions and methods of the present invention, as well as many of the optional ingredients suitable for use herein, are described in detail hereinafter.

The term "instant" and/or "on demand" as used herein refers to the respiratory preparation providing relief of one or more symptoms that is being treated, prevented, alleviated, ameliorated, inhibited, or mitigated within 20 minutes of application, alternatively within 15 minutes of application, alternatively within 10 minutes of application, alternatively within 5 minutes of application, alternatively within 2 minutes of application, alternatively within 1 minute of application. Additionally, on demand allows the user to provide relief of the user's symptoms as often as needed.

The term "pharmaceutical actives" as used herein refers to an active that is or can be registered by a Health Organization or agency as treating cough or listed as a monograph.

The term "oral compositions" as used herein refers to compositions in a form that is deliverable to a mammal in need via the oral cavity, mouth, throat, nasal passage or combinations thereof. Nonlimiting examples include liquid compositions, beverage, supplemental water, pills, soft gels, tablets, capsules, gel compositions, foam compositions, saline wash and combinations thereof. Liquid compositions, gel compositions can be in a form that is directly deliverable to the mouth and throat. These compositions and/or preparations can be delivered by a delivery device selected from droppers, pump, sprayers, liquid dropper, saline wash delivered via nasal passageway, cup, bottle, liquid filled gel, liquid filled gummy, center filled gum, chews, films, center filled lozenge, gum filled lozenge, pressurized sprayers, atomizers, air inhalation devices, liquid filled compressed tablet, liquid filled gelatin capsule, liquid filled capsule, squeezable sachets, power shots, and other packaging and equipment, and combinations thereof. The sprayer, atomizer, and air inhalation devices can be associated with a battery or electric power source.

All weights, measurements and concentrations herein are measured at 25° C. on the composition in its entirety, unless otherwise specified.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The composition, preparations and methods of the present invention can comprise, consist of, or consist essentially of, the essential elements and limitations of the invention described herein, as well as any additional or optional ingredients, components, or limitations described herein or otherwise useful in compositions intended for use or consumption by mammals preferably consumption or use by humans.

Respiratory Preparation

The present invention is a respiratory preparation. In one embodiment the respiratory preparation comprises a film forming agent; and a thickening agent. The preparation provides on demand relief. The preparation can work to physically coat the mouth and throat creating a soothing barrier over the epithelial cells that line the throat layer. The preparation can additionally, reduce inflammation and relieve minor pain associated with a cough and/or sore throat. Preferably the respiratory preparation would not contain a pharmaceutical active.

The preparation can be in a delivery device that is convenient and easy to carry and can be used as often as needed. In one embodiment the preparation is a discreet preparation. In one embodiment the preparation is delivered to a site of treatment with the delivery device. Preferably the site of treatment is the mouth and/or throat and/or esophagus. The delivery device can be selected from the group consisting of pump, spray, liquid dropper, cup, bottle, liquid filled gel, liquid filled gummy, center filled gum, chews, films, center filled lozenge, gum filled lozenge, liquid filled compressed tablet, liquid filled gelatin capsule, liquid filled capsule, squeezable sachets, power shots, and combinations thereof.

The respiratory preparation as described herein having a viscosity from about 100 centipoise (cP) to about 600 cP, from about 150 cP to about 400 cP, from about 180 cP to about 300 cP, from about 200 cP to about 275 cP, from about 220 cP to about 250 cP as measured according to ASTM Method No. D4016.

The respiratory preparation as described herein having a density from about 0.5 grams/milliliter (g/ml) to about 5 g/ml, from about 0.8 g/ml to about 4 g/ml, from about 1.0 g/ml to about 3 g/ml, from about 1.05 g/ml to about 2 g/ml, from about 1.1 g/ml to about 1.5 g/ml as measured according to ASTM Method No. D1475-98.

The respiratory preparation as described herein having a surface tension from about 30 milliNewton/meter (mN/m) to about 90 mN/m, from about 35 mN/m to about 80 mN/m, from about 40 mN/m to about 75 mN/m, from about 45 mN/m to about 70 mN/m, from about 50 mN/m to about 65 mN/m as measured according to ASTM Method No. D1331.

In one embodiment the preparation is an oral composition. The oral composition can be selected from the group consisting of liquid compositions, nasal compositions, beverage, supplemental water, gel compositions, foam compositions, pills, tablets, soft gels or capsules, and combinations thereof.

The preferred pH range of the preparation is from about 1 to about 7, from about 2 to about 6.5, from about 2 to about 5 and from about 2.6 to about 4.7.

Film Forming Agent

In an embodiment, the preparation comprises a film forming agent. When present the preparation comprises from about 0.01% to about 60%, alternatively from about 0.1% to about 40%, alternatively from about 1% to about 30%, alternatively from about 2% to about 20%, alternatively from about 3% to about 15%, by weight of the preparation.

The film forming agent can aid in coating and providing a moisturizing and/or hydration benefit that relieves the cough on contact and/or provides aid in healing the mouth and/or throat.

Nonlimiting examples of film forming agents include polyethylene oxide, polyhydric alcohols, polyhydroxyl alcohols, polyethylene glycol, muco-adhesive polymers, hydrating agents, fatty acids, surfactants including anionic, cationic, and zwitterionic, whey protein, soy protein, micro-particulated whey protein, milk fat, vegetable fat, fat, edible oil, cocoa butter, tapioca starch, polyglycerol, poloxamer, carboxymethylcellulose sodium, xanthan gums, carageenans, alginates, cyclomethicone, sodium hyaluronate, sodium lactate, tracetin, triethanolamine, starches, biopolymers, and mixtures thereof. Nonlimiting examples of hydrating agents include, humectants including but not limited to polyols, xylitol, maltitol, polydextrose, urea, lactic acid. Preferably the film forming agents include muco-adhesive polymers, hydrating agents, polyethylene glycol, polyethylene oxide and mixtures thereof.

Benefit Agent

The preparation can comprise a benefit agent. When present the preparation comprises from about 0.01% to about 30%, alternatively from about 0.03% to about 25%, alternatively from about 0.05% to about 20%, alternatively from about 1% to about 15%, alternatively from about 1.5% to about 10%, by weight of the preparation.

The benefit agent can provide cooling and warming benefit to the mouth and/or throat, signal to the user that the preparation has reached the area of the mouth and/or throat where the cough is generated and can aid in providing immediate relief of the cough.

Nonlimiting examples of benefit agents include cooling agents, warming agents, flavoring agents, salivating agents, and combinations thereof. Nonlimiting examples of cooling agents include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-ethoxyphenyl)-p-menthane-3-carboxamide), WS-5 (Ethyl-3-(p-menthane-3-carboxamido)acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International, cis & trans p-Menthane-3,8-diols (PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl(2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5).

Nonlimiting examples of warming agents include TK 1000, TK 1 mM, Heatenol—Sensient Flavors, Optaheat—Symrise Flavors, Cinnamon, Polyethylene glycol, Capsicum, Capsaicin, Curry, FSI Flavors.

Nonlimiting examples of flavoring agents include natural flavoring agents, artificial flavoring agents, artificial extracts, natural extracts and combination thereof. Nonlimiting examples of flavoring agents include: Vanilla, honey lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème Brule, caramel, caramel nut, butter, butter toffee, caramel toffee, aloe Vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, and mixtures thereof.

Nonlimiting examples of salivating agents include formula (I):

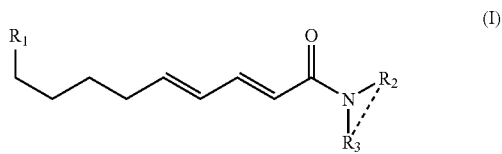

wherein $R_1$ represents C1-C2 n-alkyl; $R_2$ is 2-methyl-1-propyl and $R_3$ is hydrogen, or $R_2$ and $R_3$ taken together is a moiety having the formula —$(CH_2)_n$— wherein n is 4 or 5, or mixtures thereof. Preferably, the salivating agent comprises a material wherein $R_2$ is 2-methyl-1-propyl and $R_3$ is hydrogen, more preferably wherein $R_1$ is C1 n-alkyl, $R_2$ is 2-methyl-1-propyl and $R_3$ is hydrogen. More preferably, the salivating agent comprises trans-pellitorin, a chemical having a structure according to formula (II):

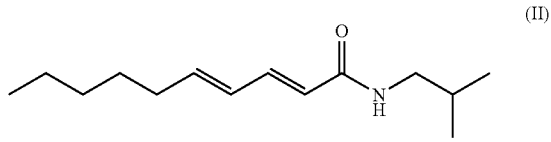 [SMILES: CCCCC/C=C/C=C/C(=O)NCC(C)C]

Thickening Agent

The respiratory preparation can further comprise a thickening agent. The thickening agent aids in coating and/or moisturizing and/or hydrating the throat and can aid in relieving the cough on contact. The thickening agent when present in the preparation comprises from about 0.01% to about 15%, alternatively from about 0.02% to about 12%, alternatively from about 0.04% to about 10%, alternatively from about 0.05% to about 5% thickening agent, by weight of the preparation. When the thickening agent is present the ratio of thickening agent to film forming agent is a ratio of from about 30 to about 1 thickening agent film forming agent, alternatively from about 20 to about 1, alternatively a ratio of from about 10 to about 1, alternatively from about 5 to about 1, alternatively from about 4 to about 1, alternatively from about 3 to about 1, alternatively from about 2 to about 1.

Nonlimiting examples of thickening agents include pregelatinized starch (corn, wheat, tapioca), pregelatinized high amylose content starch, pregelatinized hydrolyzed starches (maltodextrins, corn syrup solids), chemically modified starches such as pregelatinized substituted starches (e.g., octenyl succinate modified starches such as N-Creamer®, N-Lite LP®, and TEXTRA®, manufactured by the National Starch Company), locust bean gum, guar gum, gellan gum, xanthan gum, gum ghatti, modified gum ghatti, tragacanth gum, carrageenan, anionic polymers derived from cellulose such as carboxymethylcellulose (CMC), sodium carboxymethylcellulose, polaxamer, and mixtures thereof.

Additional Component

The respiratory preparation can further comprise at least one additional component. When present the preparation comprises from about 0.1% to about 20% of an additional component, by weight of the preparation, alternatively from about 0.5% to about 15%, alternatively from about 1% to about 10%, alternatively from about 1.5% to about 5%, alternatively from about 2% to about 4% of an additional ingredient, by weight of the preparation.

Nonlimiting Examples of an additional component includes, tea extract, Vitamin A, Vitamin C, Vitamin B, Vitamin D, carotenoid, rosemary, rosemary extract, caffeic acid, coffee extract, tumeric extract, curcumin, blueberry extract, grapeseed extract, rosemaric acid, antioxidant, amino acid, enzyme, prebiotic, probiotic, andrographis extract, 1-tryptophan, *Allium sativum*, herbal remedies, vitamins, supplements, antioxidants, natural ingredients, minerals, energy boosting ingredients, sleep aids, immune system boosting agents, colorant, preservative, fragrance, flavorant, fruit extract, a salivating agent, a salivating stimulator, and combinations thereof.

The preferred form of Vitamin C for use in the preparation is as ascorbic acid or the equivalent of a salt of ascorbic acid or the equivalent of a derivative of ascorbic acid. The vitamin C may either be in an immediate release form or a sustained release form.

Vitamin A and carotene can be obtained from either animal or vegetable sources. The vitamin A can be in the form of vitamin A, retinol, retinyl palmitate, retinyl acetate, retinyl proprionate, beta-carotene, alpha carotene, beta-cryptoxanthin, and mixtures thereof.

Nonlimiting examples of Vitamin D include Vitamin D3 (cholecalciferol), Vitamin D2 (ergocalciferol) and combinations thereof. Additional, nonlimiting examples also include metabolites of Vitamin D, including calcidiol, calcitriol, and combinations thereof. The Vitamin D, including cholecalciferol, ergocalciferol, calcidiol and calcitriol, may be derived from synthetic or natural sources. Vitamin D, including cholecalciferol and calcitriol, may be sourced from an extract of solanum glaucophyllum (malacoxylon), trisetum flavescens (goldhafer) or cestrum diurnum. Both the pure, Vitamin D and/or glycosides of the Vitamin D, may be used.

Tea extract is a polyphenol. Nonlimiting examples of extracts includes *Camellia sinensis*. Nonlimiting sources of tea extract for use in the present invention are black tea, white tea, oolong tea, and/or green tea.

When present, the preparation comprises from about $10^6$ to $10^{12}$ colony forming unit (cfu) of a probiotic, and alternatively from about $10^6$ to $10^{10}$ cfu of a probiotic. The probiotic component can be a lactic acid bacteria. Preferably the probiotic is selected from the group consisting of bacteria of the genera *Bacillus, Bacteroides, Bifidobacterium, Enterococcus* (e.g., *Enterococcus faecium*), *Lactobacillus*, and *Leuconostoc*, and combinations thereof. In another embodiment of the invention, the probiotic is selected from bacteria of the genera *Bifidobacterium, Lactobacillus*, and combinations thereof.

Non-limiting examples of lactic acid bacteria suitable for use herein include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum*, and *Pediococcus cerevisiae*, or mixtures thereof, preferably *Lactobacillus salivarius, Bifidobacterium infantis*, or mixtures thereof.

Prebiotics which are useful include beet pulp, carob bean, psyllium, citrus pectin, rice bran, locust bean, fructooligosaccharide, inulin, oligofructose, galactooligosaccharide, citrus pulp, mannanoligosaccharides, arabinogalactan, lactosucrose, glucomannan, lactulose, polydextrose, apple pomace, tomato pomace, carrot pomace, *cassia* gum, xanthan gum, gum karaya, gum talha, gum arabic, cellulose, hemicellulose, cellulose ethers, lignin and combinations thereof.

As used herein, the andrographis is a plant of the genus *Andrographis*, having a limited number of species within this genus largely present in Asia. Only a few of the species are medicinal. In one embodiment, the plant is of the species *Andrographis paniculata*, which may be referenced as Kalmegh in Ayurvedic medicine.

Coffee extract is a polyphenol. The main constituent of coffee extract is coffeic acid. When coffee extract is present nonlimiting sources of coffee extract include coffee, coffee bean, coffee berry, and/or coffee fruits. When coffeic acid is present nonlimiting sources of coffeic acid include coffee bean, coffee fruits, coffee, tea, berries, rosemary extract, and/or grapes extract.

Turmeric extract is a polyphenol. Turmeric extract is a spice which comprises a main active compound that is curcumin. Curcumin is a bioactive polyphenol plant pigment. Nonlimiting source of turmeric extract for use in the present invention is turmeric.

Blueberry extract is a polyphenol. The blueberry extract is rich in anthocyanins which display antioxidant activity.

Grapeseed extract is a polyphenol. The grape seed extract is rich in procyanidins which display antioxidant activity. Nonlimiting source of grapeseed extract for use in the present invention is grape seed.

A "carotenoid" is a class of pigments occurring in the tissues of higher plants, algae, bacteria and fungi. They are usually yellow to deep red. When a carotenoid is present, the carotenoid is selected from the group consisting of betacarotene, lutein, astaxanthin, zeaxanthin, bixin, lycopene, and mixtures thereof.

Amino acids are the "building Blocks" of the body. Besides building cells and repairing tissue, they form antibodies to combat invading bacteria & viruses; they are part of the enzyme & hormonal system; they carry oxygen throughout the body and participate in muscle activity. When an amino acid is present, the amino acid is selected from the group consisting of Lysine, Taurine, Histidine, Carnosine, Alanine, Cysteine, and mixtures thereof.

When an antioxidant is present, the antioxidant is selected from the group consisting of Vitamin E, CoQ10, and mixtures thereof. Major dietary sources of vitamin E are vegetable oils, margarine and shortening, with nuts, seeds, whole grains and wheat germ providing additional sources. "Vitamin E" includes eight different chemical forms: four tocopherols and four tocotrienols. The most biologically active form of vitamin E is alpha-tocopherol.

Nonlimiting examples of preservative include but are not limited to benzoalkonium chloride, EDTA, benzyl alcohol, potassium sorbate, parabens, benzoic acid, sodium benzoate, and mixtures thereof.

Sweeteners

The respiratory preparation may comprise a sweetener to provide sweetness and to provide some body and thickness. When a sweetener is present in the preparation, the preparation may comprise from about 0.0001% to about 40% sweetener, from about 0.0001% to about 20% sweetener, alternatively from about from about 0.0001% to about 10% sweetener, alternatively from about from about 0.0001% to about 2% sweetener and alternatively from about 0.05% to about 1.0% sweetener, all by weight of the preparation. The sweeteners can be artificial sweeteners.

Non-limiting examples of artificial sweeteners are selected from the group consisting of sodium saccharine, acesulfame potassium, sucralose, aspartame, monoammonium glycyrrhizinate, neohesperidin dihydrochalcone, thaumatin, neotame, cyclamates, stevia, and mixtures thereof. Generally, such artificial sweeteners are solids when used in sweetening the respiratory preparations.

When an artificial sweetener is present, the preparation may comprise from about 0.0001% to about 5% artificial sweetener, from about 0.0001% to about 3.5% artificial sweetener, alternatively from about from about 0.0001% to about 2.0% artificial sweetener, alternatively from about from about 0.0001% to about 1.0% artificial sweetener and alternatively from about 0.05% to about 1.0% artificial sweetener, all by weight of the preparation.

Optional Ingredients

The preparations can comprise a wide range of optional ingredients. Nonlimiting examples of optional ingredients include antimicrobial metal salts, optional mildness enhancers, optional stabilizers, abrasives, biological additives, chemical additives, chelants, denaturants, drug astringents, excipient, emulsifiers, topical analgesics, a second film former, fragrance compounds, humectants, opacifying agents, plasticizers, propellants, reducing agents, solvents, foam boosters, stabilizers, hydrotropes, solubilizing agents, suspending agents (non-surfactant), a solvent, viscosity increasing agents (aqueous and non-aqueous), sequestrants, buffers, keratolytics, and the like, and combinations thereof. Nonlimiting examples of antimicrobial metal salts include zinc, iron, copper, silver, tin, bismuth, and combinations thereof. Nonlimiting examples of excipients include sorbitol, maltitol, mannitol, and combinations thereof. Unless otherwise specified, the preparations may optionally comprise one or more given optional ingredients at concentrations ranging from about 0.001% to about 99%, alternatively from about 0.01% to about 80%, alternatively from about 0.01% to about 50%, alternatively from about 0.01% to about 10%, all by weight of the preparation.

Methods of Use

As used herein, the term "orally administering" and/or "administering" with respect to the human/mammal means that the human/mammal ingests or is directed to ingest, or does ingest, or deliver, or chew, or drink, or spray, or place in mouth, one or more of the present respiratory preparations. The human/mammal may be directed to deliver the respiratory preparation to the site that the human/mammal intends to treat for example the mouth and/or throat. The human/mammal may be directed to ingest or deliver or chew, or drink, or spray, or place in mouth the preparation, such direction and or delivery may be that which instructs and/or informs the human that use of the preparation may and/or will provide relief from the respiratory symptom (e.g., symptomatic relief, whether temporary or permanent) for example, relief from coughing and/or sore throat. The relief can be instant or on demand. For example, such direction may be oral direction (e.g., through oral instruction from, for example, a physician, pharmacist, or other health professional), radio or television media (e.g., advertisement), or written direction (e.g., through written direction from, for example, a physician, pharmacist, or other health professional (e.g., scripts), sales professional organization (e.g., through, for example, marketing brochures, pamphlets, or other instructive paraphernalia), written media (e.g., internet, electronic mail, or other computer-related media)), and/or packaging associated with the composition (e.g., a label present on a delivery device holding the preparation). As used herein "written" means through words, pictures, symbols, and/or other visible or tactile descriptors. Such information need not utilize the actual words used herein, for example, "respiratory", "symptom", or "mammal", but rather use of words, pictures, symbols, tactile means, and the like conveying the same or similar meaning are contemplated within the scope of this invention.

In a further embodiment, the respiratory preparation is directed to methods of treating and providing cough relief on demand comprising administering a preparation as described herein to a mammal in need of such treatment. As further used herein, "treatment" and/or "providing relief" with respect to cough relief means that administration of the referenced respiratory preparation prevents, alleviates, ameliorates, inhibits, or mitigates one or more symptoms of the cough relief.

In a further embodiments, the respiratory preparation can also be directed to methods of "prevention" including preventing a cough or its associated symptoms from occurring in a mammal, for example when the mammal is predisposed to acquiring the symptoms of coughing, inhibiting the onset of coughing or its associated symptoms; and/or alleviating, reversing, or curing the coughing episode or its associated symptoms. Additionally, in a further embodiments, the respiratory preparation can also be directed to methods of "prevention" including preventing cough or its associated symptoms from occurring in a human/mammal, for example when the human/mammal is in an environment or location where coughing is undesired such as church, movie, theatre, sporting arena, or field or other entertainment venue.

Administration may be on an as-needed or as-desired basis, for example, once-monthly, once-weekly, or daily, including multiple times daily, for example, at least once daily, from one to about forty times daily, from one to about thirty times daily, from one to about twenty times daily, from one to about fifteen times daily, from one to about ten times daily, from about two to about four times daily, or about three times daily.

The amount of respiratory preparation administered may be dependent on a variety of factors, including the general quality of health of the mammal, age, gender, weight, or severity of symptoms.

Method of Making

The respiratory preparations may be prepared by any known or otherwise effective techniques suitable for providing a composition that provides a therapeutic benefit. In one embodiment the respiratory preparation is made by combining film forming agent with a solvent. The combined ingredients are then added to a mixing vessel containing flavors, film forming agent, solvents, sweeteners, preservatives and mixed until homogenous. Next the preparation is packaged into spray bottles. Preferably the spray bottles comprise polyethylene terephthalate (PET).

In an alternative embodiment, the respiratory preparation is made by combining the film forming agent with a solvent. In a separate vessel the following are then added to a mixing vessel containing flavoring agent, film forming agent, solvents, sweeteners, preservatives, heating to and blending until uniform. The combined ingredients from the mixing vessel are added while above 60° C. to a mold, and the film forming agent and solvent are injected into the center of the mold, and do not harden. The shell layer will harden, leaving the film forming agent and solvent in the center. Next the preparation is ejected from the mold and wrapped in a suitable delivery device.

Kit

In a further embodiment, the invention can comprise a kit. The kit can comprise: a delivery device and a respiratory preparation contained in said delivery device; wherein said respiratory preparation comprising a film forming agent; a thickening agent; and wherein said respiratory preparation provides on demand cough relief. The kit may further comprise at least one additional component. The kit may further comprise at least one optional ingredient. The kit may also comprise an additional respiratory preparation in a full size, a sample size or both. The kit may further comprise an additional composition that coordinates with the respiratory preparation that is comprised within the delivery device or attached to the outside of the delivery device. For example if the preparation contained in the delivery device is a preparation for the relief from coughing, the coordinating composition and/or preparation may be for congestion. As well, if the preparation in the delivery device is a preparation for coughing the coordinating preparation and or composition may be for runny nose, nasal or chest congestion, sneezing, pressure, headache, aches, fever, or sore throat. As well, if the preparation in the delivery device is a preparation for coughing the coordinating preparation and/or composition may be a vitamin. The kit could also comprise facial tissue in combination with the respiratory preparation, a hand sanitizer in combination with the respiratory preparation or a day time kit or a night time kit that depends on the coordinating preparation, additional ingredient and/or optional ingredient that is combined with the respiratory preparation. The kit may further comprise a coupon, rebate, or advertisement. The kit may further comprise a set of instructions. These instructions may also include illustrations.

Experimental Studies

Experimental Study 1

Study Objectives

The primary objective of this study was to obtain the data needed to determine the appropriate design (including sample size and choice of comparator) for a full-scale study to evaluate the effectiveness of the respiratory preparations in reducing cough frequency (measured via objective cough counts) during a 4-hour observation period relative to the chosen comparator (either a water control or reference therapy).

Secondary Objectives were to Obtain a Preliminary Assessment of:

the effectiveness of the respiratory preparations in reducing cough frequency (measured via objective cough counts) relative to a water control and reference therapy; and the effectiveness of the respiratory preparations in reducing perceived cough frequency and severity relative to a water control and reference therapy;

Tertiary Objectives were to Obtain a Preliminary Assessment of:

the effectiveness of the respiratory preparations in providing faster, longer, and better perceived cough relief relative to a water control; and the effectiveness of the respiratory preparations in providing better perceived coating of the throat relative to a water control.

Quaternary Objectives are to Obtain a Preliminary Assessment of:

the effectiveness of the respiratory preparations in reducing cough frequency (measured via objective cough counts) relative to a no treatment control;

the effectiveness of the respiratory preparations in reducing perceived cough frequency and severity relative to a no treatment control;

the effectiveness of the water control in reducing cough frequency (measured via objective cough counts) relative to a no treatment control; and the effectiveness of the water control in reducing perceived cough frequency and severity relative to a no treatment control.

Investigational Plan

Study Design

This was a randomized, parallel, partially single-blind, single-center, controlled study in adult males and females who were suffering from symptoms of common cold/flu but were otherwise healthy. Potential subjects were screened against the Inclusion/Exclusion criteria. Subjects who qualified to participate in the study were randomized into 1 of 5 test groups: Respiratory preparation 1 (approximately 40 subjects), Respiratory preparation 2 (approximately 40 subjects), a reference therapy (approximately 40 subjects), a water control (approximately 40 subjects), and a no treatment control (approximately 10 subjects).

Qualified subjects remained at the study site throughout a 4-hour observation period. Subjects assigned to the no treatment control received no treatment during the 4-hour observation period. Subjects assigned to the reference therapy took a single dose of the 30 mg dextromethorphan HBr solution under supervision of study personnel at the beginning of the 4-hour observation period. Subjects in all other groups used their test product each time they felt the urge to cough throughout the 4-hour observation period.

Continuous digital video and audio recordings were obtained throughout the 4-hour observation period. (The video and digital audio recordings were viewed/listened to by trained observers at a later time in order to obtain objective counts of cough bouts, individual coughs, and test product usage for each subject.)

At 1, 2, 3, and 4 hours, subjects self-assessed the frequency and severity of their cough in the context of the previous hour. Subjects completed a Final Questionnaire immediately after completing the 4-hour observation period and after completing the 4-hour subjective assessment of cough frequency and severity.

Selection of Study Population

A target of approximately 170 adult male and female subjects suffering cold or flu-like symptoms and experiencing cough were enrolled and completed this study.

Inclusion Criteria

To be considered eligible for enrollment into this study, subjects must have:

1. been generally healthy by report and review of medication/medical history;

2. been at least 18 years of age and not older than 65 years of age;

3. if female, had a negative result for a urine pregnancy test administered at screening and reported they were not actively trying to conceive or lactating;

4. reported they were experiencing cold/flu-like symptoms with the first signs occurring no more than 10 days prior to Visit 1;

5. experienced at least 3 cough bouts during a 30 minute period at screening;

6. been willing and able to refrain from eating, drinking, smoking, and putting anything into their mouth other than their assigned test product for the duration of Visit 1;

7. been willing and able to sit in a room, staying alert and awake, with limited interaction for a period of approximately 4½ hours;

8. read, understood, signed, and received a copy of the Informed Consent and Confidentiality/Non-Disclosure Agreement prior to initiation of the study procedures.

Visit 1

Screening/Enrollment

In order to qualify for enrollment into the study, subjects must have experienced at least 3 cough bouts in the 30 minute period. They received a kitbox labeled with their assigned randomization number. With the exception of the no treatment control group, the kitboxes contained test product and usage instructions.

4-Hour Observation Period

Subjects remained on site in the room in which they were screened throughout a 4-hour observation period. They were instructed to open their assigned kitbox and directed to use their assigned test product according to the instructions. Subjects assigned to the no treatment control received no test product to use during the 4-hour observation period. Subjects assigned to the reference therapy took a single dose of the 30 mg dextromethorphan hydrobromide solution under supervision of study personnel at the beginning of the 4-hour observation period. Subjects in all other groups used their test product each time they felt the urge to cough throughout the 4-hour observation period. Continuous digital video and audio recordings were obtained throughout the 4-hour observation period. At 1, 2, 3, and 4 hours, subjects self-assessed the frequency and severity of their cough in the context of the previous hour. Subjects were instructed to refrain from eating, drinking, smoking, and putting anything into their mouth other than their test product and to refrain from all activities with the exception of reading and paperwork. Subjects were allowed to use the restroom, if necessary. Study personnel monitored subjects to ensure they were alert and complied with study procedures and to answer any questions that subjects may have had.

Efficacy Assessments

Continuous Digital Video and Audio Recordings

Digital video and audio recordings were obtained continuously throughout the 4-hour observation period. The video and audio recordings were made simultaneously and as part of the same digital file, for each subject using a single recording device. A network camera (IP camera) was the recording device used to create each digital audio/video file. For consistency, each observation room was outfitted with the same recording equipment.

The feeds from each network camera ran to a central personal computer which was running software recording each network camera's audio/video feed to an individual digital file, later viewable by a media player software application.

Trained observers viewed and listened to subjects' recordings in order to obtain objective counts of cough bouts, individual coughs, and test product usage. The number of individual coughs was quantified by counting the number of explosive sounds. An explosive sound is always present in a cough and is the characteristic sound we recognize as cough. In a series of individual coughs, each expiration was counted as 1 cough. The number of cough bouts was quantified by counting the number of series of individual coughs. Consecutive cough bouts were separated by inspirations.

Test Groups

Method of Assigning Subjects to Test Groups

Subjects were randomly assigned to test groups in a 1:4:4:4:4 ratio (no treatment control, water control, reference therapy, respiratory preparation 1, respiratory preparation 2). Subjects were assigned randomization numbers (501-755) in increasing numerical order as they qualified for the study. Randomization numbers were randomly assigned to test groups in blocks of size 17. Subjects were identified throughout the study by unique subject numbers assigned as the subjects presented to the study site.

Description of Test Groups/Usage Instructions

FIG. 1 is Table 1 and shows a description of the test groups and brief usage instructions.

Identity of Test Product

A reference therapy of 30 mg DexM that is a commercially available product was overlabeled and packed. Test products and usage instructions were contained in a kitbox labeled with the randomization number, study number, caution statements, and other information as required by internal regulatory and clinical SOPs. Bottles were labeled with study number, applicable caution and warning statements, usage directions, and other information as dictated by internal regulatory requirements and clinical standard operating procedures.

Product Compliance

Subjects were sequestered on site and used the test products on site. Subjects assigned to the reference therapy were dosed under supervision of study personnel. All subjects were monitored through digital video and audio streams. This was a randomized, parallel, partially single-blind controlled study.

Efficacy and Safety Variables

Efficacy Variables

Number of Coughs in the 4-Hour Observation Period:
the number of coughs manually counted by the trained observer in the digital video and audio recording of the 4-hour observation period.

Number of Coughs in Each Hourly Interval:
the number of coughs manually counted by the trained observer in each 1-hour interval of the digital video and audio recording of the 4-hour observation period.

Number of Cough Bouts in the 4-Hour Observation Period:
the number of cough bouts manually counted by the trained observer in the digital video and audio recording of the 4-hour observation period.

Number of Cough Bouts in Each Hourly Interval:
the number of cough bouts manually counted by the trained observer in each 1-hour interval of the digital video and audio recording of the 4-hour observation period.

Perceived Cough Frequency:
Subjects' responses to the question: "How OFTEN have you coughed in the last hour?" Assessed at each of 1, 2, 3, and 4 hours.

Perceived Cough Severity:
Subjects' responses to the question: "How SEVERE has your cough been in the last hour?" Assessed at each of 1, 2, 3, and 4 hours.

Perceived Onset of Cough Relief:
Subjects' responses to the question: "On average, HOW SOON after using the test product did it START TO RELIEVE YOUR COUGH?" Assessed after the 4-hour observation period.

Perceived Duration of Cough Relief:
Subjects' responses to the question: "On average, FOR HOW LONG after using the test product did you FEEL SOME RELIEF OF YOUR COUGH?" Assessed after the 4-hour observation period.

Perceived Level of Cough Relief
Subjects' responses to the question: "On average, HOW WELL did the test product RELIEVE YOUR COUGH after you used it?" Assessed after the 4-hour observation period.

Perceived Level of Coating of the Throat
Subjects' responses to the question: "On average, HOW WELL did you FEEL YOUR THROAT WAS COATED after using the test product?" Assessed after the 4-hour observation period.

Percent of Evaluable Subjects

Respiratory preparation 1 and 2 were each compared versus the No Treatment Control, Water Control, and Reference Therapy and the Water Control was compared versus the No Treatment Control with respect to percent of randomized subjects who were excluded from all evaluable subjects' analysis populations. These comparisons were made on a two-sided basis at a type I error rate of 0.10 using Fisher's exact test. No adjustments were made to control the experiment-wise type I error rate.

Demographic and Baseline Characteristics

Descriptive statistics were calculated for both analysis populations (randomized subjects and evaluable subjects) by experimental group and displayed in tabular form. Respiratory preparation 1 and 2 were each compared versus the No Treatment Control, Water Control, and Reference Therapy for both analysis populations (randomized subjects and evaluable subjects). The Water Control was also compared versus the No Treatment Control for both populations. These comparisons were made on a two-sided basis at a type I error rate of 0.10 using the Wilcoxon Rank Sum test (Age, Number of Bouts, Sore Throat, Rhinorrhea, Nasal Congestion, Cough, and Malaise), Fisher's exact test (Sex), and Pearson's $\chi^2$ test (Race). No adjustments were made to control the experiment-wise type I error rate.

Efficacy Variables

Statistical Comparisons

The primary comparisons of interest were Respiratory preparation 1 and 2 versus the Water Control and Reference Therapy with respect to Number of Coughs in the 4-hour observation period.

Of secondary interest were comparisons of Respiratory preparation 1 and 2 versus the Water Control and Reference Therapy with respect to:

Number of Coughs in each 1-hour interval of the 4-hour observation period;

Number of Cough Bouts in the 4-hour observation period;

Number of Cough Bouts in each 1-hour interval of the 4-hour observation period;

Perceived Cough Frequency and Perceived Cough Severity at each of 1, 2, 3, and 4 hours AND at the average across 1, 2, 3, and 4 hours.

Of tertiary interest were comparisons of Respiratory preparation 1 and 2 versus the Water Control with respect to Perceived Onset of Cough Relief, Perceived Duration of Cough Relief, Perceived Level of Cough Relief, and Perceived Level of Coating of the Throat.

Of quaternary interest were comparisons of Respiratory preparation 1 and 2 and the Water Control versus the No Treatment Control with respect to:

Number of Coughs in the 4-hour observation period;

Number of Coughs in each 1-hour interval of the 4-hour observation period;

Number of Cough Bouts in the 4-hour observation period;

Number of Cough Bouts in each 1-hour interval of the 4-hour observation period;

Perceived Cough Frequency and Perceived Cough Severity at each of 1, 2, 3, and 4 hours AND at the average across 1, 2, 3, and 4 hours.

For comparisons of the experimental groups with respect to Number of Coughs, Number of Cough Bouts, Perceived Cough Frequency, and Perceived Cough Severity (all time points), the following one-sided hypotheses were tested using the Wilcoxon Rank Sum test:

Number of Usages

Descriptive statistics were calculated for the evaluable subjects analysis populations by experimental group (Respiratory preparation 1 and 2 and Water Control) and displayed in tabular form.

Respiratory preparation 1 and 2 were each compared versus the Water Control with respect to number of usages for the evaluable subjects analysis populations. These comparisons were made on a two-sided basis at a type I error rate of 0.10 using the Wilcoxon Rank Sum test. No adjustments were made to control the experiment-wise type I error rate.

Study Subjects

Disposition of Subjects

One hundred seventy-five subjects were randomized to the 5 treatment groups. Of these, 2 subjects did not complete the study and were dropped due to loud and disruptive behavior (Subject 0023; Water Control) and a voluntary withdrawal (Subject 0150; Water Control) FIG. 2 is Table 2 including a description of the Number of Subjects randomized to Treatment Groups.

Efficacy Evaluation 0.1. Data Sets Analyzed

Twelve subjects were excluded from all evaluable subjects' analysis populations: 6 Water Control; 3 Reference Therapy; 1 Respiratory preparation 1 and 2 Respiratory preparation 2. Eleven subjects were excluded because more than 10% of their cough data in the 4-hour observation period was not gradable due to audio/video outages:

One subject was excluded because the subject did not comply with product usage instructions: Subject 0179 (Water Control).

A significantly ($\alpha<0.10$) higher percent of subjects were excluded in the Water Control treatment group compared with Respiratory preparation 1.

Three subjects were excluded from the evaluable subjects' analysis populations for Number of Coughs, Number of Bouts, and Number of Usages for 1 or 2 hourly intervals because more than 10% of the cough/usage data for that interval was not gradable due to audio/video outages:

Four subjects were excluded from the evaluable subjects' analysis populations for Number of Coughs, Number of Bouts, and Number of Usages for one hourly interval because more than 10% of the cough/usage data for that interval was not gradable due to their being out of the viewing room:

Three subjects were excluded from the evaluable subjects' analysis populations for all the efficacy variables for 1 or 2 Hourly Subjective Assessments (and the average Hours 1-4) because it was more than 20% off-schedule:

Two subjects were excluded from the evaluable subjects' analysis populations for an efficacy variable on an Hourly Subjective Assessment (and the average Hours 1-4) due to missing data:

Demographic and Other Baseline Characteristics

Evaluable subjects were generally well balanced on the demographic characteristics. The overall mean age was 35.7 years; the majority of subjects were either Black (53%) or Caucasian (45%) with an almost even representation of males (55%) and females (45%).

Randomized Subjects

There were statistically significant differences ($\alpha<0.10$) for Respiratory preparation 1 versus Water Control and Reference Therapy with respect to Number of Bouts, Respiratory preparation 2 versus Reference Therapy with respect to Rhinorrhea, and Water Control versus No Treatment Control with respect to Nasal Congestion.

Evaluable Subjects

There were statistically significant differences ($\alpha<0.10$) for Respiratory preparation 1 versus Water Control with respect to Number of Bouts and Nasal Congestion, Respiratory preparation 1 versus Reference Therapy with respect to Number of Bouts, and Water Control versus No Treatment Control with respect to Nasal Congestion. All other two-sided comparisons of Respiratory preparation 1 and 2 versus the No Treatment Control, Water Control, and Reference Therapy and of the Water Control versus the No Treatment Control with respect to the demographic and other baseline characteristics were not significant at $\alpha=0.10$.

Efficacy Results and Tabulations of Individual Subject Data
Analysis of Efficacy
Respiratory Preparation 1 Vs. No Treatment Control FIG. 3 is Table 3 which includes a description of the summary of efficacy results for the Respiratory preparation 1 vs. No Treatment Control.

The number of coughs, cough bouts and perceived cough frequency experienced by subjects who received Respiratory preparation 1 were significantly lower ($\alpha<0.10$) than the No Treatment Control at Hours 2, 3, 4 and 1-4.

Perceived cough severity experienced by subjects who received Respiratory preparation 1 was significantly lower ($\alpha<0.10$) than the No Treatment Control at Hours 1, 2, 3, 4 and 1-4.

Respiratory Preparation 1 Vs. Water Control

FIG. 4 is Table 4 which includes a description of the summary of efficacy results for the Respiratory preparation 1 vs. Water Control.

Perceived Cough Frequency experienced by subjects who received Respiratory preparation 1 were significantly lower ($\alpha<0.10$) than the Water Control at Hour 4.

Perceived Cough Severity experienced by subjects who received Respiratory preparation 1 was significantly lower ($\alpha<0.10$) than the Water Control at Hours 2, 4 and 1-4.

Perceived Onset of Cough Relief, Perceived Level of Cough Relief and Perceived Level of Throat Coating experienced by subjects who received Respiratory preparation 1 were significantly higher ($\alpha<0.10$) than the Water Control at the final observation period (after 4 hours).

Respiratory Preparation 1 Vs. Reference Therapy

FIG. 5 is Table 5 which includes a description of the all one-sided comparisons of Respiratory preparation 1 versus the Reference Therapy with respect to the efficacy parameters were not significant at $\alpha=0.10$.

Respiratory Preparation 2 Vs. No Treatment Control

FIG. 6 is Table 6 which includes a description of the summary efficacy results for the Respiratory preparation 2 vs. No Treatment Control.

The number of coughs, cough bouts, perceived cough frequency and perceived cough severity experienced by subjects who received Respiratory preparation 2 were significantly lower ($\alpha<0.10$) than the No Treatment Control for all evaluations (at Hours 1, 2, 3, 4 and 1-4).

Respiratory preparation 2 vs. Water Control

FIG. 7 is Table 7 which includes a description of the Summary efficacy results for the Respiratory preparation 2 vs. Water Control.

Number of Coughs and Perceived Cough Frequency experienced by subjects who received Respiratory preparation 2 were significantly lower ($\alpha<0.10$) than the Water Control at Hours 2, 3, 4 and 1-4.

Number of Cough Bouts experienced by subjects who received Respiratory preparation 2 was significantly lower ($\alpha<0.10$) than the Water Control at Hours 2, 4 and 1-4.

Perceived Cough Severity experienced by subjects who received Respiratory preparation 2 was significantly lower ($\alpha<0.10$) than the Water Control at Hours 2 and 4.

Perceived Onset of Cough Relief, Perceived Level of Cough Relief and Perceived Level of Throat Coating experienced by subjects who received Respiratory preparation 2 were significantly higher ($\alpha<0.10$) than the Water Control at the final observation period (after 4 hours).

Respiratory Preparation 2 Vs. Reference Therapy

FIG. 8 is Table 8 which includes a description of the summary efficacy results for the Respiratory preparation 2 vs. Reference Therapy.

Number of Coughs and Cough Bouts experienced by subjects who received Respiratory preparation 2 were significantly lower ($\alpha<0.10$) than the Reference Therapy at Hours 1 and 2.

Efficacy Conclusions

Significantly fewer usages of both Respiratory preparation 1 and 2 were noted overall (1-4 hours) and at specific time points during the study compared with water control.

Overall (Hours 1-4), Respiratory preparation 1 showed superiority over the No Treatment Control with significantly fewer number of coughs, cough bouts and perceived cough frequency. Further, at the final observation period, Perceived Onset of Cough Relief, Perceived Level of Cough Relief and Perceived Level of Throat Coating were significantly lower in subjects in the Respiratory preparation 1 group compared to the Water Control.

Overall and for each time point of the analysis, Respiratory preparation 2 showed superiority over the No Treatment Control with significantly fewer number of coughs, cough bouts, perceived cough frequency and perceived cough severity. When compared with the Water Control, Respiratory preparation 2 showed superiority with a fewer Number of Coughs and Perceived Cough Frequency over all time points and overall except within the $1^{st}$ hour and fewer Number of Cough Bouts overall and hours 2 and 4, individually. Further, at the final observation period, Perceived Onset of Cough Relief, Perceived Level of Cough Relief and Perceived Level of Throat Coating were significantly were significantly lower in subjects in the Respiratory preparation 2 group compared to the Water Control.

Interestingly, simply lubricating the throat (Water Control) showed benefit on cough measures (Number of Coughs, Cough Bouts, Perceived Cough Frequency and Perceived Cough Severity) compared to No Treatment Control at all time points evaluated.

For the primary comparisons of interest, there was a statistically significant difference with respect to reduced Number of Coughs in the 4-hour observation period for Respiratory preparation 2 compared to the Water Control, but not for Respiratory preparation 1. Overall (Hours 1-4), there was no difference in number of coughs for either device compared to Reference Therapy.

Of secondary interest were comparisons of Respiratory preparation 1 and 2 versus the Water Control and Reference Therapy with respect to the Number of Coughs and Cough Bouts in each 1-hour interval of the 4-hour observation period, Number of Cough Bouts in the 4-hour observation period and Perceived Cough Frequency and Perceived Cough Severity at each of 1, 2, 3, and 4 hours and at the average across 1, 2, 3, and 4 hours. For Respiratory preparation 1 perceived cough frequency and perceived cough severity were significantly less at Hour 4 and hours 2, 4, and 1-4, respectively, that the Water Control. There was no difference in any other comparison of Respiratory preparation 1 vs the Water Control or any comparison with the Reference Therapy. For Respiratory preparation 2 vs the Water Control, Number of Coughs and Perceived Cough Frequency were significantly less at Hours 2, 3, 4, and 1-4, the Number of Cough Bouts were significantly less at Hours 2, 4, and 1-4, and Perceived Cough Severity was significantly less at Hours 2 and 4. For Respiratory preparation 2 vs the Reference Control, Number of Coughs and Cough Bouts were significantly less at Hours 1 and 2.

Of tertiary interest were comparisons of Respiratory preparation 1 and 2 versus the Water Control with respect to Perceived Onset of Cough Relief, Perceived Duration of Cough Relief, Perceived Level of Cough Relief, and Perceived Level of Coating of the Throat. Perceived Onset of Cough Relief, Perceived Level of Cough Relief and Perceived Level of Throat Coating experienced by subjects who received Respiratory preparation 1 and 2 were significantly higher ($\alpha<0.10$) than the Water Control at the final observation period.

Of quaternary interest were comparisons of Respiratory preparation 1 and 2 and the Water Control versus the No Treatment Control with respect to the Number of Coughs and Number of Cough Bouts, Perceived Cough Frequency and Perceived Cough Severity at each individual time point and overall Hours 1-4. The number of coughs, cough bouts and perceived cough frequency experienced by subjects who received Respiratory preparation 1 were significantly lower ($\alpha<0.10$) than the No Treatment Control at Hours 2, 3, 4 and 1-4. Perceived cough severity experienced by subjects who received Respiratory preparation 1 was significantly lower ($\alpha<0.10$) than the No Treatment Control at Hours 1, 2, 3, 4 and 1-4. The number of coughs, cough bouts, perceived cough frequency and perceived cough severity experienced by subjects who received Respiratory preparation 2 were significantly lower ($\alpha<0.10$) than the No Treatment Control for all evaluations (at Hours 1, 2, 3, 4 and 1-4).

Overall these Results Demonstrate the Following:
Consistent evidence of efficacy across all parameters for Respiratory preparation 2 relative to the water control more than Respiratory preparation 1. Large differences were observed for Respiratory preparation 2 relative to the water control.

Experimental Study II

This Experimental study is designed to evaluate using gamma scintigraphy the retention of a 5 mL volume of the respiratory preparation in the oral cavity and oropharynx when administered to the back of the tongue via a syringe. Two formulations will be tested.

Study Objectives

The primary objectives of this study are to evaluate: the total volume of an respiratory preparation retained in the oral cavity and oropharynx over a period of 1 hour following oral administration in healthy human volunteers using gamma scintigraphy, and the volume of the respiratory preparation retained in the oropharynx at the earliest measurable time period (as permitted by the method) following oral administration in healthy human volunteers using gamma scintigraphy.

Secondary Objectives are to Evaluate:

The secondary objectives of this study are to evaluate: the total volume of the respiratory preparation retained in the esophagus over a period of 1 hour following oral administration in healthy human volunteers using gamma scintigraphy, and the total volume of a commercial device retained in the oral cavity, oropharynx and esophagus over a period of 1 hour following oral administration in healthy human volunteers using gamma scintigraphy.

Investigational Plan

Study Design

This will be an open label single use, randomized, parallel study in adult healthy males.

Potential subjects will be screened against the Inclusion/Exclusion criteria at Visit 1 such that a minimum of 40 are enrolled into the study and scheduled for Visit 2. A minimum of 32 subjects who qualify to continue in the study at Visit 2 will be administered a single usage of either the investigational or commercial device by Study Personnel. Retention of the radiolabeled devices in the oral cavity, oropharynx and esophagus will be monitored using gamma scintigraphy for 1 hour post-usage.

Study Population

Selection of Study Population

Inclusion Criteria

To be considered eligible for enrollment into this study, subjects must:
a. be generally healthy as determined by medical history, medication history, physical examination (including resting vital signs), ENT examination, and routine clinical laboratory tests (including CBC and blood chemistry);
b. be male, between the ages of 18 and 40 years, inclusive;
c. have fasted during the previous 8 hours;
d. have read, understood, signed, and received a copy of the Informed Consent, HIPAA authorization and Confidentiality/Non-Disclosure Agreement prior to initiation of study procedures;
e. be willing to refrain from gum, hard candies, caffeine, alcohol, tobacco/smoking/nicotine, cough suppressants, throat lozenges, or nasal, throat or lung inhalants for 24 hours prior to Visit 2;
f. be willing to refrain from exercise for 24 hours prior to Visit 2;
g. be willing and able to tolerate measurement procedures for the Respiratory preparation;
h. be willing and able to tolerate restricted movement, such as will be required during the scintigraphy procedures; and
i. seem, in the opinion of the Investigator, motivated and capable of participating in the study;

Continuance Criteria

To be eligible for continued participation in the study at Visit 2, subjects must not have:
a. any clinically significant changes to their health since the last visit as determined by a review of their medical history, concomitant medications, and resting vital signs by qualified personnel;
b. taken any prescription or nonprescription medications within the past 7 days or within 5 half-lives, whichever is longer (exceptions are nonprescription non-steroidal anti-inflammatory medication allowed up to 72 hours prior to this visit);
c. evidence of current respiratory tract infection, active allergic rhinitis or respiratory congestion;
d. consumed gum, hard candies, alcohol, caffeine, tobacco/nicotine, cough suppressants, throat lozenges, or used nasal, throat or lung inhalants within the previous 24 hours;
e. exercised within the previous 24 hours; or
f. had anything to eat or drink within the previous 2 hours.

Scintigraphy

Subjects will report to the study site at their designated time for Visit 2 no more than 30 days after Visit 1 and after refraining from eating and drinking for at least 2 hours. Subjects will be instructed to drink 4 ounces water and to refrain from additional eating and drinking until after they have completed the 1-hour scintigraphic acquisition.

Study Personnel will prepare the bottles/syringes containing the assigned radiolabeled device for use in an appropriate manner and document in the batch record.

Control (Commercially Available Product) (Reference Medical Device)

Approximately 1 hour after drinking the 4 ounces of water, subjects will be administered 2 sprays of the radiolabeled reference medical device into the mouth for a total volume of approximately 0.35 mL. The reference medical device used is one intended for relief of dry mouth. Subjects will be instructed NOT to swallow for 60 seconds after the last spray. Study Personnel will notify subjects when swallowing can resume and record all swallows to the extent possible throughout the 1-hour scintigraphic acquisition. Within approximately 15 seconds of the last spray, the subject will be positioned with their chest facing the detector of the gamma camera and their head in a left lateral position, in contact with the front of the detector. Study Personnel will weigh the bottle containing the Reference Medical Device before and after administration. In addition, the bottle will be counted in the dose calibrator before and after administration. Subjects will then undergo the procedures for scintigraphic acquisition as described below.

Subjects will be positioned with their chest facing the detector of the gamma camera and their head in a left lateral position and in contact with the front of the detector. Subjects will have a syringe containing 5 mL of the radiolabeled respiratory preparation inserted into their mouth and will be instructed to close their mouth around the syringe. A 15-second static image will be obtained.

Approximately 1 hour after drinking the 4 ounces of water, Study Personnel will instruct subjects to open their mouth and will place 5 mL of the radiolabeled device on the back of the subject's tongue. Subjects will be instructed to swallow immediately after administration of the 5 mL. Study Personnel will record all swallows to the extent possible throughout the 1-hour scintigraphic acquisition. Within approximately 15 seconds of the administration, the subject will be positioned with their chest facing the detector of the gamma camera and their head in a left lateral position, in contact with the front of the detector. Study Personnel will weigh the syringe containing the respiratory preparation before and after administration. In addition, the syringe will be counted in the dose calibrator before and after administration. Subjects will then undergo the procedures for scintigraphic acquisition as described below.

Scintigraphy Acquisition

Scintigraphic acquisition will start approximately 15 seconds after device administration and will end 1 hour 15 seconds after device administration. A dynamic image set consisting of twelve continuous 15-second frames immediately followed by 54 continuous 30 second frames will be acquired in the first 30 minutes. Note that the dynamic imaging may be interrupted for a short interval (less than 30 seconds) during the last 15 minutes of this 30 minute period in the event that subjects experience discomfort. Every attempt will be made to acquire a continuous 30 minute interval, and if any interruption in imaging occurs, these frames will be excluded from data analysis.

Once the dynamic image set is complete, the subject will be removed from the detector and allowed to relax while sitting near the gamma camera. The subject will be repositioned in front of the detector to obtain a 30-second static image every 5 minutes for the next 30 minutes. External radioactive sources (fiducials) will be placed on the subject (e.g. at the mid brow line and on the chin or elsewhere as deemed appropriate by Study Personnel) in order to account for subject movement and repositioning during static imaging sequences. Another external radioactive source may be used to outline the head, neck and shoulder as they appear within the field of view of the gamma camera.

The subject will remain as quiet and motionless as possible and with their head in contact with the detector throughout the 30-minute dynamic image set and throughout each 30-second static image. Restraint tape may be used as a reminder to the subject to remain motionless during imaging. The subject will remain quiet and minimize any movement such as standing, walking, etc. during the time in between imaging.

Identity of Commercially Available Product)(Reference Medical Device) and Respiratory preparation. FIG. 9 is Table 9 and shows a description of the respiratory preparation and Reference Medical Device.

Radiolabeling Procedures

The radionuclide used in this study is Technetium-99m ($^{99m}$Tc), in the form of $^{99m}$Tc sodium-carboxymethyl cellulose ($^{99m}$Tc—NaCMC). Study personnel will radiolabel the sodium carboxymethyl cellulose with $^{99m}$Tc following Sponsor approved procedures documented in Sponsor approved batch records. Study personnel will add the radiolabeled sodium-carboxymethyl cellulose to the Reference Medical Device and respiratory preparation on each study day (within 24 hours of administration to subjects). They will add the radiolabel in an appropriate volume to respiratory preparation and Reference Medical Device. They will also perform a confirmation of the radiolabel and activity. The homogeneity of each formulation will be determined and recorded in the respective master batch records. Preparation of the radiolabeled Reference Medical Device and respiratory preparation and handling radiopharmaceuticals will follow Sponsor approved procedures documented in Sponsor approved batch records.

Device/Respiratory Preparation Administration

Study Personnel will administer to each subject a single usage of the appropriate device/respiratory preparation, based on the randomization provided by the Sponsor, and document in master batch records or source documents. Study Personnel will administer the devices/respiratory preparation as follows:

Respiratory Preparation:

5 mL of the preparation will be placed on the back of the subject's tongue using a 10 cc syringe. Subjects will be instructed to swallow immediately after administration of the 5 mL.

Reference Medical Device™:

2 sprays of the device will be directed into the subject's mouth. Subjects will be instructed NOT to swallow for at least 60 seconds after administration. Before and after administration of the Reference Medical Device or Respiratory Preparation, the container (syringe or bottle) will be weighed in order to determine the total weight delivered to the subject.

Radioactivity Exposure

Subjects will receive one single administration of Reference Medical Device or respiratory preparation, which will contain the radioactive marker.

Effectiveness Observations and Measurements

Scintigraphy Analysis

The raw radiation counts will be archived on computer disk and/or optical disk after being aligned and having removed the external markers from the images using ScinCam data acquisition software (Siemens Cameras 1 and 2: ScinCam Version 2.10, Build 001, Siemens Camera 3: ScinCam Version 2.00 Build 042, GE Camera: ScinCam Version 2.96+, Build 008) and ScinWin data analysis software (ScinWin Version 2.95, Build 013, GammaForge, Louisville, Ky.). Scintigraphic data analysis for each radionuclide will be performed on specialized Nuclear Mac software (Version 5.6) as follows: The sequential computer generated images will be reviewed for each subject and three regions of interest will be drawn to represent the oral cavity, oropharynx, and esophagus using Nuclear Mac software. All counts will be corrected for radioactivity decay and background. Elapsed time along with the radionuclide half life will be used to correct for radioactivity decay. For the background correction, an arbitrary region will be selected away from the throat on each image. The total number of radiation counts in this region will be divided by the total number of pixels, and this count per pixel will be subtracted from each pixel in each anatomical region of interest.

Volume of Reference Medical Device retained for each combination of subject, image, and region of interest will be calculated by: corrected count÷concentration of radiation in the Reference Medical Device (sum of the adjusted counts across all regions of interest in the first 15-second image obtained after administration of the device÷the volume of Reference Medical Deviceadministered in mL).

Volume of respiratory preparation retained for each combination of subject, image, and region of interest will be calculated by: corrected count÷concentration of radiation in the respiratory preparation (sum of the adjusted counts across all regions of interest in the 15-second image obtained prior to administration of the respiratory preparation divided by volume of respiratory administered in mL).

Primary Endpoints
Of Primary Interest Will be:
  Area under the curve from 0 to 60 minutes for volume of respiratory preparation retained in the oral cavity following administration and subject positioning,
  Area under the curve from 0 to 60 minutes for volume of respiratory preparation retained in the oropharynx following administration and subject positioning, and
  Volume of respiratory preparation retained in the oropharynx during the first 15-second frame following administration and subject positioning.

Secondary Endpoints
Of Secondary Interest Will be:
  Area under the curve from 0 to 60 minutes for volume of Reference Medical Device retained in the oral cavity following administration and subject positioning,
  Area under the curve from 0 to 60 minutes for volume of Reference Medical Device retained in the oropharynx following administration and subject positioning, and
  Area under the curve from 0 to 60 minutes for volume of Reference Medical Device retained in the esophagus following administration and subject positioning.
  Area under the curve from 0 to 60 minutes for volume of respiratory preparation retained in the esophagus following administration and subject positioning.

Experimental Study III

In the present trial, the respiratory preparation is being delivered to the back of the throat in a stream via a spray bottle. The study is designed to evaluate the retention of the respiratory preparation in the oral cavity, oropharynx, and esophagus using gamma scintigraphy.

The primary objective of this study is to evaluate the retention of a respiratory preparation in the oropharynx following oral administration in healthy human volunteers using gamma scintigraphy.

Investigational Plan
Study Design

This will be a single usage, open label study in 16 adult healthy males. Sixteen subjects who qualify to continue in the study at Visit 2 will be administered a single usage of the respiratory preparation by Study Personnel. Retention of the radiolabeled respiratory preparation in the oral cavity, oropharynx and esophagus will be monitored using gamma scintigraphy for 1 hour post-usage.

Inclusion Criteria

To be considered eligible for enrollment into this study, subjects must:

a. be generally healthy as determined by medical history, medication history, physical examination (including resting vital signs), ENT examination, and routine clinical laboratory tests (including CBC and blood chemistry);

b. be male, between the ages of 18 and 40 years, inclusive;

c. have fasted during the previous 8 hours;

d. have read, understood, signed, and received a copy of the Informed Consent, HIPAA authorization and Confidentiality/Non-Disclosure Agreement prior to initiation of study procedures;

e. demonstrate that they are able to tolerate administration of the respiratory preparation;

f. be willing to refrain from gum, hard candies, caffeine, alcohol, tobacco/smoking/nicotine, cough suppressants, throat lozenges, or nasal, throat or lung inhalants for 24 hours prior to Visit 2;

g. be willing to refrain from exercise for 24 hours prior to Visit 2;

h. be willing and able to tolerate restricted movement, such as will be required during the scintigraphy procedures; and i. seem, in the opinion of the Investigator, motivated and capable of participating in the study;

Study Procedures

Visit 2 Scintigraphy

Subjects will report to the study site at their designated time for Visit 2 Study site. no more than 10 days after Visit 1 and after refraining from eating and drinking for at least 2 hours. Subjects will be instructed to drink 4 ounces water and to refrain from additional eating and drinking until after they have completed the 1-hour scintigraphic acquisition. Study Personnel will prepare the assigned spray bottle containing the radiolabeled respiratory preparation for use in an appropriate manner and document in the batch record. In order to correct for radiation attenuation through the neck, Study Personnel will administer a single spray of the radiolabeled respiratory preparation into a plastic bag. Subjects will be positioned with their chest facing the detector of the gamma camera and their head in a left lateral position and in contact with the front of the detector. Study Personnel will hold the radioactive bag on the side of the subject's neck away from the detector and obtain a 1-minute static image. The subject will then be removed from the detector, the radioactive bag will be positioned at the same distance from the detector, and a second 1-minute static image will be obtained. Approximately 1 hour after drinking the 4 ounces of water, subjects will be administered 3 sprays of radiolabeled respiratory preparation to the back of the throat for a total volume of approximately 0.48 mL. Subjects will be instructed to not swallow for 60 seconds after the last spray. Study Personnel will notify subjects when swallowing can resume and record all swallows to the extent possible throughout the 1-hour scintigraphic acquisition. Within approximately 20 seconds of the last spray, the subject will be positioned with their chest facing the detector of the gamma camera and their head in a left lateral position, in contact with the front of the detector. Scintigraphic acquisition will start approximately 20 seconds after the last spray and will end 1 hour 20 seconds after the last spray. A dynamic image set consisting of sixty continuous 30-second frames will be acquired in the first 30 minutes. Note that the dynamic imaging may be interrupted for a short interval (less than 30 seconds) during the last 15 minutes of this 30 minute period in the event that subjects experience discomfort. Every attempt will be made to acquire a continuous 30 minute interval, and if any interruption in imaging occurs, these frames will be excluded from data analysis. Once the dynamic image set is complete, the subject will be removed from the detector and allowed to relax while sitting near the gamma camera. The subject will be repositioned in front of the detector to obtain a 30-second static image every 5 minutes for the next 30 minutes. External radioactive sources (fiducials) will be placed on the subject (e.g. at the mid brow line and on the chin or elsewhere as deemed appropriate by study personnel) in order to account for subject movement and repositioning during static imaging sequences. Another external radioactive source may be used to outline the head, neck and shoulder as they appear within the field of view of the gamma camera. The subject will remain as quiet and motionless as possible and with their head in contact with the detector throughout the 30-minute dynamic image set and throughout each 30-second static image. Restraint tape may be used as a reminder to the subject to remain motionless. At the end of the scintigraphic acquisition period, adverse device effects will be assessed, study closeout procedures will be completed and subjects will be compensated for their participation in the study Respiratory Preparation Groups
Identity of Respiratory Preparation FIG. 10 is Table 10 and shows a description of the respiratory preparation.

Preparation of Respiratory Preparation at the Site

The Investigator will be responsible for the radiolabelling of sodium carboxymethyl cellulose with $^{99m}$Tc, acquiring the aqueous $^{111}$In-DTPA, and assembly of the test articles. Preparation of the radiolabeled respiratory preparation and handling radiopharmaceuticals will follow Sponsor approved procedures documented in Sponsor approved batch records. The radionuclide used in this study is Technetium-99m ($^{99m}$Tc), in the form of $^{99m}$Tc sodium-carboxymethyl cellulose ($^{99m}$Tc—NaCMC) and Indium DTPA ($^{111}$In-DTPA)[2]. The radiolabeled sodium-carboxymethyl cellulose will be prepared following Sponsor approved procedures documented in Sponsor approved batch records. The radiolabeled sodium-carboxymethyl cellulose will be added to the respiratory preparation on each study day, in an appropriate volume. All respiratory preparations will be prepared within 12 hours of dosing, and confirmation of radiolabel and activity will be completed.

Respiratory Preparation Administration

The actuator will be properly primed prior to use and subject assignment to bottles will be documented in master batch records or source documents. Prior to and following administration of the respiratory preparation, the bottle will be weighed in order to determine the total weight delivered to the subject. All subjects will receive 1 administration of three target sprays without delay for a total of approximately 0.48 ml of radiolabeled respiratory preparation delivered to the back of the throat by Study Personnel. Subjects will be asked not swallow for at least 60 seconds after administration of the respiratory preparation.

Radioactivity Exposure

The respiratory preparation will be administered once to each subject, and this administration will contain radioactive markers.

Effectiveness Observations and Measurements
Scintigraphy Analysis

The raw radiation counts for each combination of subject, pixel, and radionuclide ($^{99m}$Tc and $^{111}$In) will be archived on computer disk and/or optical disk after being aligned and having removed the external markers from the images using ScinCam data acquisition software and ScinWin data analysis software (GammaForge, Louisville, Ky.). Scintigraphic data analysis for each radionuclide will be performed on specialized Nuclear Mac software as follows: The sequential computer generated images will be reviewed for each subject and three regions of interest will be drawn to represent the oral cavity, oropharynx, and esophagus using Nuclear Mac software. All counts will be corrected for radioactivity decay, background, and attenuation of radiation through the neck. Elapsed time along with the radionuclide half life will be used to correct for radioactivity decay. For the background correction, an arbitrary region will be selected away from the throat on each image. The total number of radiation counts in this region will be divided by the total number of pixels, and this count per pixel will be subtracted from each pixel in each anatomical region of interest. The attenuation correction will be made using the 1-minute static images captured prior to administration of the respiratory preparation (one image with the subject in position at the detector and the radioactive bag positioned at the neck away from the camera and one image of the radioactive bag at the same distance without the subject). Fraction retention in each of the regions of interest will be calculated by summing the counts across all the regions in the first complete frame of data acquisition and dividing the count in each region of interest by this sum. Fraction retained versus time curves will be generated allowing area-under-curve (AUC) and rate constants to be computed for each radionuclide, $^{99m}$Tc and $^{111}$In.

Primary Endpoints

Of primary interest will be area under the curve from 0 to 1 hour for percent of the respiratory preparation retained in the oropharynx, estimated via $^{99m}$Tc—NaCMC counts and denoted AUC(0-1; oropharynx; $^{99m}$Tc—NaCMC).

Secondary Endpoints
Of Secondary Interest Will be:
  Area under the curve from 0 to 1 hour for percent of the respiratory preparation retained in the oropharynx, estimated via $^{111}$In-DTPA counts and denoted AUC(0-1; oropharynx; $^{111}$In-DTPA)
  Area under the curve from 0 to 1 hour for percent of the respiratory preparation retained in the oral cavity, estimated via $^{99m}$Tc—NaCMC counts and denoted AUC(0-1; oral cavity; $^{99m}$Tc—NaCMC).
  Area under the curve from 0 to 1 hour for percent of the respiratory preparation retained in the oral cavity, estimated via $^{111}$In-DTPA counts and denoted AUC(0-1; oral cavity; $^{111}$In-DTPA)
  Area under the curve from 0 to 1 hour for percent of the respiratory preparation retained in the esophagus, estimated via $^{99m}$Tc—NaCMC counts and denoted AUC(0-1; esophagus; $^{99m}$Tc—NaCMC).
  Area under the curve from 0 to 1 hour for percent of the respiratory preparation retained.

Efficacy Results and Tabulations of Individual Subject Data
Analysis of Efficacy (Per-Protocol)

As per protocol, the area under the retained fraction versus time curve from 0 to 1 hour was calculated for the PP population. The descriptive statistics and 95% confidence intervals for the mean of each scintigraphy parameter are provided in FIG. 11 which is Table 11 for Technetium-99m and FIG. 12 which is Table 12 for Indium DTPA. A graphical depiction of the area under the retained volume versus time curve from 0 to 1 hour by region of interest is provided in FIG. 13. The listing of mean area under the retained fraction versus time curve from 0 to 1 hour by subject is provided in FIG. 11.

Primary Efficacy Endpoint Results

The mean area under the retained fraction versus time curve from 0 to 1 hour for the total oropharynx was 6.01 minutes, with a 95% confidence interval of 3.91 to 8.10 minutes using $^{99m}$Tc—NaCMC (FIG. 11).

Secondary Efficacy Endpoint Results

Total Oropharynx

The mean area under the retained fraction versus time curve from 0 to 1 hour for the total oropharynx was 5.83 minutes, with a 95% confidence interval of 3.66 to 7.99 minutes using $^{111}$In-DTPA (FIG. 12).

Oral Cavity

The mean area under the retained fraction versus time curve from 0 to 1 hour for the oral cavity was 3.36 minutes (95% confidence interval [2.06, 4.67]) using $^{99m}$Tc—NaCMC (FIG. 11) and 2.69 minutes (95% confidence interval [1.68, 3.70]) using $^{111}$In-DTPA (FIG. 12).

Esophagus

The mean area under the retained fraction versus time curve from 0 to 1 hour for the esophagus was 1.52 minutes (95% confidence interval [1.15, 1.89] using $^{99m}$Tc—NaCMC (FIG. 11) and 1.41 minutes (95% confidence interval [1.05, 1.77]) using $^{111}$In-DTPA (FIG. 12).

Additional Efficacy Endpoint Results

An additional analysis of the mean area under the retained fraction versus time curve from 0 to 1 hour for the proximal oropharynx showed means of 1.83 minutes (95% confidence interval [1.22, 2.45]) for $^{99m}$Tc—NaCMC (FIG. 11) and 1.63 minutes (95% confidence interval [1.09, 2.17]) using $^{111}$In-DTPA (FIG. 12.

Analysis of Adhoc Efficacy Endpoints

Retention volumes for the Technetium-99m data were calculated from the mass retained in each of the regions of interest: oral cavity, esophagus and total oropharynx. The area under the retained volume versus time curve from 0 to 1 hour was calculated for the PP population. A graphical depiction of the area under the retained volume versus time curve from 0 to 1 hour by region of interest is found in FIG. 13.

Efficacy Conclusions

There were no differences in the comparison of $^{99m}$Tc—CMC vs $^{111}$In-DTPA retention in the regions of interest selected for observation: oral cavity (mouth), total oropharynx, or esophagus. The mean area under the retained fraction versus time curve from 0 to 1 hour was the shortest in the esophagus with a time of approximately 1.5 minutes, doubling to about 3.5 minutes in the oral cavity and nearly doubling again for the total oropharynx. Retained volumes ranged from about 0.75 mL×minutes in the esophagus, to about 1.7 mL×minutes in the oral cavity to 3 mL×minutes in the total oropharynx.

Discussion and Overall Conclusions

The results of this study suggest that the respiratory preparation was retained in the mouth, oropharynx and esophagus as measured by gamma scintigraphy using both $^{99m}$Tc—NaCMC and $^{111}$In-DTPA methods. Coating in the mouth and on the tongue seen on the scintigraphic images and quantitative data is suspected to be largely due to the administration technique of spraying into the distal mouth. There were no differences in the comparison of $^{99m}$Tc—CMC vs $^{111}$In-DTPA retained fraction AUCs in the regions of interest selected for observation: oral cavity (mouth), total oropharynx, or esophagus. When the additional anatomical region of proximal oropharynx was observed, there was some radioactive substance retention, but not as great as the total oropharynx even when the coating per unit area was computed. The number of pixels used for the final count evaluation determined the unit area. The formulation was influenced by gravity with a resulting drainage into and down the esophagus. Swallowing was monitored, but did not have any observable influence on the retention of the formulation in the oropharynx. There was no scintigraphic image evidence of any formulation entering the larynx or trachea for any of the 16 subjects. The image acquisition during the first 30 minutes allowed no movement of the subjects, but after the initial 30 minutes of image acquisition the subjects were permitted to move (not standing) away from the scintillation camera surface. In some subjects, there was an observed clearance that was enhanced compared to the previous 30-minute stationary acquisition. There were significant differences in the retained fraction AUC's for Tc-99m-CMC when comparing the oral cavity, total oropharynx and esophagus. There was definite coating with retention on the oropharynx surfaces with pooling above the epiglottis. The pooling observation enhanced the appearance of retained fraction of the formulation. Therefore pooling does involve coating the total oropharynx surface.

EXAMPLES

The following examples further describe and demonstrate embodiments within the scope of the present invention. They are given for the purpose of illustration and are not to be construed as limitations of the present invention.

Below are illustrated various non-limiting examples of respiratory preparations of the present invention.

Examples 1-4

| Ingredient | #1 | #2 | #3 | #4 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.50 | 0.50 | 0.50 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | 0.45 | 0.45 | 0.45 | 0.45 |
| Polyethylene Oxide, NF | 0.15 | 0.05 | 0.25 | — |
| Benzoic Acid, USP | 0.15 | 0.15 | 0.15 | 0.15 |
| Carbomer 956 | — | — | — | 0.15 |
| FLV Tart Honey Lemon N&A 455115 | 0.98 | 0.98 | 1.01 | 1.01 |
| Cooling Agent (WS-23) | 0.02 | 0.02 | — | — |
| Cooling Agent #10 | 0.03 | 0.03 | — | — |
| Total | 100.00 | 100.00 | 100.00 | 100.00 |
| Surface Tension (mN/m) | 61.4 | 50.4 | 66.9 | 49.2 |
| Density g/ml | 1.12 | 1.09 | 1.10 | 1.12 |
| pH | 4.5 | 4.7 | 4.6 | 4.6 |
| Brookfield Viscosity (cP) | 255.2 | 200.1 | 277.2 | 222.3 |

Examples 5-8

| Ingredient | #5 | #6 | #7 | #8 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.50 | 0.30 | 0.50 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | 0.45 | 0.45 | — | 0.45 |
| Polyethylene Oxide, NF | 0.15 | 0.25 | — | 0.15 |
| Benzoic Acid, USP | 0.15 | 0.65 | 0.15 | 0.15 |
| Carbomer 956 | 0.10 | — | 0.15 | 0.25 |
| FLV Tart Honey Lemon N&A 455115 | 0.98 | 0.98 | 0.98 | 0.98 |
| Cooling Agent (WS-23) | 0.02 | — | 0.02 | 0.02 |
| Cooling Agent #10 | 0.03 | — | 0.03 | 0.03 |
| Total | 100.00 | 100.00 | 100.00 | 100.00 |
| Surface Tension (mN/m) | 64.7 | 53.5 | 62.9 | 40.0 |
| Density g/ml | 1.12 | 1.09 | 1.10 | 1.12 |
| pH | 4.5 | 4.2 | 4.2 | 4.2 |
| Brookfield Viscosity (cP) | 255.2 | 180.5 | 251.2 | 263.2 |

Examples 9-12

| Ingredient | #9 | #10 | #11 | #12 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.50 | 0.10 | 0.25 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | — | 0.20 | — | — |
| Polyethylene Oxide, NF | — | 0.50 | — | — |
| Benzoic Acid, USP | 0.15 | 0.65 | 0.15 | 0.15 |
| Carbomer 956 | 0.05 | 0.40 | 0.30 | 0.10 |
| FLV Tart Honey Lemon N&A 455115 | 0.98 | 0.98 | 0.98 | 0.78 |
| Cooling Agent (WS-23) | 0.02 | 0.02 | 0.02 | — |
| Cooling Agent #10 | 0.03 | 0.03 | 0.03 | 0.03 |
| Total | 100.00 | 100.00 | 100.00 | 100.00 |
| Surface Tension (mN/m) | 58.9 | 44.8 | 45.7 | 63.1 |
| Density g/ml | 1.12 | 1.09 | 1.10 | 1.12 |
| pH | 4.5 | 4.7 | 4.6 | 4.6 |
| Brookfield Viscosity (cP) | 210.1 | 232.0 | 260.2 | 241.5 |

Examples 13-16

| Ingredient | #13 | #14 | #15 | #16 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.50 | — | 0.50 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | — | 0.45 | — | — |
| Polyethylene Oxide, NF | — | 0.05 | — | — |
| Benzoic Acid, USP | 0.15 | 0.15 | 0.15 | 0.15 |
| Carbomer 956 | 0.10 | 0.30 | 0.20 | 0.50 |
| FLV Tart Honey Lemon N&A 455115 | 0.98 | 0.98 | 0.98 | 1.10 |
| Cooling Agent (WS-23) | 0.02 | 0.02 | 0.02 | — |
| Cooling Agent #10 | 0.03 | 0.03 | 0.03 | — |
| Total | 100.00 | 100.00 | 100.00 | 100.00 |
| Surface Tension (mN/m) | 61.2 | 40.6 | 64.1 | 41.4 |
| Density g/ml | 1.12 | 1.12 | 1.12 | |
| pH | 4.5 | 4.5 | 4.5 | 4.7 |
| Brookfield Viscosity (cP) | 245.6 | 200.12 | 275.2 | 301.4 |

Examples 17-20

| Ingredient | #17 | #18 | #19 | #20 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.30 | — | 0.50 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | 0.45 | 0.45 | 0.45 | 0.45 |
| Polyethylene Oxide, NF | 0.15 | 0.15 | 0.13 | 0.10 |
| Benzoic Acid, USP | 0.15 | 0.15 | 0.15 | 0.15 |
| Carbomer 956 | 0.20 | 0.50 | — | — |
| FLV Tart Honey Lemon N&A 455115 | 0.98 | 0.98 | 0.98 | 0.98 |
| Cooling Agent (WS-23) | 0.02 | 0.02 | 0.02 | 0.02 |
| Cooling Agent #10 | 0.03 | 0.03 | 0.03 | — |
| Total | 100.00 | 100.00 | 100.00 | 100.00 |
| Surface Tension (mN/m) | 52.8 | 40.5 | 62.3 | 64.5 |
| pH | 4.6 | 4.6 | 4.5 | 4.5 |
| Brookfield Viscosity (cP) | 199.5 | 200.1 | 235.4 | 250.2 |

Examples 21-24

| Ingredient | #21 | #22 | #23 | #24 |
|---|---|---|---|---|
| | Amount (ww %) | | | |
| USP Water | QS | QS | QS | QS |
| Sucralose | 0.08 | 0.08 | 0.08 | 0.08 |
| Sodium CMC Type 7 HOF | 0.30 | — | 0.50 | 0.50 |
| Propylene Glycol, USP | 15.00 | 15.00 | 15.00 | 15.00 |
| Sodium Benzoate NF, FCC | 0.10 | 0.10 | 0.10 | 0.10 |
| Sorbitol | 10.00 | 10.00 | 10.00 | 10.00 |
| Polyoxyl 40 Stearate | 0.45 | 0.45 | 0.45 | 0.45 |
| Polyethylene Oxide, NF (900,000 mw) | 0.15 | — | — | — |
| Polyethylene Oxide, NF 600,000 mw | — | 0.15 | — | — |
| Polyethylene Oxide, NF 300,000 mw | — | — | 0.15 | — |
| Polyethylene Oxide, NF 200,000 mw | — | — | — | 0.15 |
| Benzoic Acid, USP | 0.15 | 0.15 | 0.15 | 0.15 |
| Carbomer 956 | — | — | — | — |

-continued

| Ingredient | #21 | #22 | #23 | #24 |
|---|---|---|---|---|
| | | Amount (ww %) | | |
| FLV Tart Honey Lemon N&A 455115 | 1.10 | 0.98 | 0.98 | 0.98 |
| Cooling Agent (WS-23) | — | 0.02 | 0.02 | 0.02 |
| Cooling Agent #10 | — | 0.03 | 0.03 | 0.03 |
| Total | 100.00 | 100.00 | 100.00 | 100.00 |
| Surface Tension (mN/m) | 64.1 | 41.4 | 52.8 | 40.5 |
| Density g/ml | 1.12 | 1.12 | 1.12 | 1.12 |
| pH | 4.5 | 4.7 | 4.6 | 4.6 |
| Brookfield Viscosity (cP) | 210.5 | 245.6 | 256.7 | 246.8 |

Examples 25-27

| Ingredient | #25 | #26 | #27 |
|---|---|---|---|
| | | Amount (ww %) | |
| USP Water | QS | QS | QS |
| Sucralose | 0.07 | 0.07 | 0.07 |
| Sodium CMC Type 7 HOF | 0.45 | 0.47 | 0.42 |
| Propylene Glycol, USP | 13.50 | 14.25 | 12.75 |
| Sodium Benzoate NF, FCC | 0.09 | 0.09 | 0.08 |
| Sorbitol | 9.00 | 9.50 | 8.50 |
| Polyoxyl 40 Stearate | 0.40 | 0.42 | 0.38 |
| Polyethylene Oxide, NF | 0.13 | 0.14 | 0.12 |
| Benzoic Acid, USP | 0.13 | 0.14 | 0.12 |
| Carbomer 956 | — | — | — |
| FLV Tart Honey Lemon N&A 455115 | 0.98 | 0.98 | 0.98 |
| Cooling Agent (WS-23) | 0.02 | 0.02 | 0.02 |
| Cooling Agent #10 | 0.03 | 0.03 | 0.03 |
| Total | 100.00 | 100.00 | 100.00 |
| Surface Tension (mN/m) | 68.2 | 66.5 | 70.5 |
| Density g/ml | 1.12 | 1.12 | 1.12 |
| pH | 4.6 | 4.6 | 4.7 |
| Brookfield Viscosity (cP) | 234.5 | 205.1 | 173.1 |

Flavor available from FSI, Cincinnati, OH, USA
Cooling agents available from Takasago International Corp., Tokyo, Japan Examples 1-13, 15-17, 19-21 and 23-27 can be made by first adding at least one half of the water, benzoic acid and sodium CMC into a clean vessel. The contents are still until the CMC disperses and hydrates. In a second separate clean vessel propylene glycol, polyoxyl 40 stearate, polyethylene oxide, sucralose, remaining water, sorbitol, sodium benzoate and flavors are added and stirred until dissolved. The two mixtures are then combined and mixed until homogenous and then placed in a delivery device comprising the material polyethylene terephthalate (PET).

Examples 14, 18 & 22 can be made by first adding water, propylene glycol, carbomer, polyoxyl 40 stearate polyethylene oxide, sorbitol, benzoic acid, sucralose, flavors and sodium benzoate into a clean vessel. The contents are stirred until all the ingredients have dissolved and hydrated.

Examples 5, 8 & 17 can be made by first adding at least one half of the water, benzoic acid and sodium CMC into a clean vessel. The contents are still until the CMC disperses and hydrates. In a second separate clean vessel propylene glycol, polyoxyl 40 stearate, polyethylene oxide, carbomer, sucralose, remaining water, sorbitol, sodium benzoate and flavors are added and stirred until dissolved. The two mixtures are then combined and mixed until homogenous and then placed in a delivery device comprising the material PET.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A respiratory preparation that targets a throat and provides cough relief in a human comprising:
    a) about 0.15% of a film forming agent wherein the film forming agent is polyethylene oxide;
    b) from about 0.1% to about 0.5% of a thickening agent wherein the thickening agent is carboxymethylcellulose;
wherein said respiratory preparation provides on demand relief and a number of coughs is reduced by at least about 40% at hour one as compared to a no treatment control; wherein the respiratory preparation does not contain a pharmaceutical active and wherein the respiratory preparation is sprayable by a spray bottle and each spray comprises less than 0.35 mL of the respiratory preparation.

2. The respiratory preparation of claim 1, comprising about 0.5% thickening agent, by weight of the preparation.

3. The respiratory preparation of claim 1, further comprising from about 0.01% to about 1% of a cooling agent by weight of the respiratory preparation.

4. The respiratory preparation of claim 3, wherein the cooling agent comprises 2-Isopropyl-N,2,3-trimethylbutyramide.

5. The respiratory preparation of claim 1, having a viscosity from about 220 cP to about 300 cP.

6. The respiratory preparation of claim 1, having a density from about 0.5 grams/milliliter (g/ml) to about 2 g/ml.

7. The respiratory preparation of claim 1, having a surface tension from about 45 milliNewton/meter (mN/m) to about 70 mN/m.

8. The respiratory preparation of claim 1, wherein said respiratory preparation further comprising a sweetener.

9. The respiratory preparation of claim 8, wherein said sweetener comprises an artificial sweetener.

10. The respiratory preparation of claim 1, wherein said oral composition is administerable at least once daily.

11. The respiratory preparation of claim 1 wherein two sprays of the respiratory preparation comprises about 0.35 mL of respiratory preparation.

12. A respiratory preparation that targets a throat and provides on demand cough relief within about 20 minutes of application in a human comprising:
    a) about 0.15% of a film forming agent, by weight of the respiratory preparation, wherein the film forming agent is polyethylene oxide;
    b) about 0.50% of a thickening agent, by weight of the respiratory preparation, wherein the thickening agent is carboxymethylcellulose;
    c) a preservative; and
    d) a sweetener;

wherein said respiratory preparation does not contain a pharmaceutical active wherein the respiratory preparation is sprayable by a spray bottle and each spray comprises less than about 0.35 mL of the respiratory preparation and wherein a number of coughs is reduced by at least about 40% at hour one as compared to a no treatment control.

13. The respiratory preparation of claim 12 wherein the sweetener is an artificial sweetener.

14. The respiratory preparation of claim 13 wherein the preservative is potassium sorbate.

15. The respiratory preparation of claim 14 further comprising benzyl alcohol.

16. The respiratory preparation of claim 12 further comprising propylene glycol.

17. The respiratory preparation of claim 12 comprising from about 12% to about 15% propylene glycol.

18. The respiratory preparation of claim 12 further comprising a cooling agent.

19. The respiratory preparation of claim 12 further comprising from about 71% to about 77% water.

20. The respiratory preparation of claim 11 wherein the respiratory preparation provides on demand cough relief within about five minutes of application.

21. The respiratory preparation of claim 12 wherein the respiratory preparation has a viscosity from about 220 cP to about 300 cP.

22. The respiratory preparation of claim 12 wherein two sprays of the respiratory preparation comprises about 0.35 mL of respiratory preparation.

23. A method of providing cough relief and sore throat relief in a human comprising: the steps of administering to a human the respiratory preparation of claim 1.

24. The method of claim 23, wherein said oral composition is administered at least once daily.

25. A method of providing cough relief and sore throat relief in a human comprising: the steps of administration to a human the respiratory preparation of claim 12.

* * * * *